United States Patent
Fu et al.

(10) Patent No.: US 11,857,726 B2
(45) Date of Patent: Jan. 2, 2024

(54) MASK SIZING TOOL USING A MOBILE APPLICATION

(71) Applicant: ResMed Pty Ltd, Bella Vista (AU)

(72) Inventors: Timothy Tsun-Fai Fu, Sydney (AU); Denis Butyletskiy, Sydney (AU); Michiel Kooij, Sydney (AU); Benjamin Peter Johnston, Sydney (AU); Robert James Hudson, Sydney (AU)

(73) Assignee: ResMed Pty Ltd

( * ) Notice: Subject to any disclaimer, the term of this patent is extended or adjusted under 35 U.S.C. 154(b) by 175 days.

(21) Appl. No.: 17/196,391

(22) Filed: Mar. 9, 2021

(65) Prior Publication Data

US 2021/0299384 A1 Sep. 30, 2021

Related U.S. Application Data

(63) Continuation of application No. 15/578,440, filed as application No. PCT/AU2016/050560 on Jun. 30, 2016, now Pat. No. 10,980,957.

(Continued)

(51) Int. Cl.
*G06K 9/00* (2022.01)
*A61M 16/06* (2006.01)
(Continued)

(52) U.S. Cl.
CPC .............. *A61M 16/06* (2013.01); *A61B 5/097* (2013.01); *A61B 5/1077* (2013.01);
(Continued)

(58) Field of Classification Search
CPC ........ G16H 10/60; G16H 15/00; G16H 40/67; G16H 80/00; G16H 20/30; G16H 40/63;
(Continued)

(56) References Cited

U.S. PATENT DOCUMENTS 4,782,832 A 11/1988 Trimble et al.
4,944,310 A 7/1990 Sullivan
(Continued)

FOREIGN PATENT DOCUMENTS

AU 2010249222 A1 6/2012
CN 1422596 A 6/2003
(Continued)

OTHER PUBLICATIONS

Chinese Office Action dated Apr. 2, 2021 for CN Application No. 2016800388955.
(Continued)

*Primary Examiner* — Alex Kok S Liew
(74) *Attorney, Agent, or Firm* — Botos Churchill IP Law LLP

(57) ABSTRACT

Apparatus and methods automate selection of patient interface(s) according to their size, such as with processing in a processor(s) or in a server(s). Image data captured by an image sensor may be received. The captured image data may contain facial feature(s) of an intended user of the patient interface. The facial features may be captured in association with a predetermined reference feature of known dimension(s). The user's facial feature(s) and the reference feature may be detected in the captured image data. Image pixel data of the image may be processed to measure an aspect of the detected facial feature(s) based on the reference feature. A patient interface size may be detected from standard patient interface sizes based on a comparison between the measured aspect of the facial feature(s) and a data record relating sizing information of the standard patient interface sizes and the measured aspect of the facial feature(s).

24 Claims, 23 Drawing Sheets

Related U.S. Application Data

(60) Provisional application No. 62/313,202, filed on Mar. 25, 2016, provisional application No. 62/186,461, filed on Jun. 30, 2015.

(51) Int. Cl.
| | |
|---|---|
| *A61M 16/00* | (2006.01) |
| *G16H 20/40* | (2018.01) |
| *G16H 40/63* | (2018.01) |
| *A61B 5/097* | (2006.01) |
| *G06V 40/16* | (2022.01) |
| *G06V 10/75* | (2022.01) |
| *G16H 30/40* | (2018.01) |
| *A61B 5/107* | (2006.01) |
| *G16H 10/60* | (2018.01) |
| *A61B 5/00* | (2006.01) |

(52) U.S. Cl.
CPC ....... *A61B 5/1079* (2013.01); *A61M 16/0051* (2013.01); *A61M 16/021* (2017.08); *G06V 10/7553* (2022.01); *G06V 40/171* (2022.01); *G16H 20/40* (2018.01); *G16H 30/40* (2018.01); *G16H 40/63* (2018.01); *A61B 5/7264* (2013.01); *A61M 2016/0661* (2013.01); *A61M 2205/3306* (2013.01); *A61M 2205/3553* (2013.01); *A61M 2205/3584* (2013.01); *A61M 2205/3592* (2013.01); *A61M 2205/50* (2013.01); *A61M 2205/505* (2013.01); *A61M 2205/52* (2013.01); *A61M 2205/6063* (2013.01); *A61M 2205/6072* (2013.01); *A61M 2230/00* (2013.01); *G16H 10/60* (2018.01)

(58) Field of Classification Search
CPC ........ G16H 50/20; G16H 40/20; G16H 10/20; G16H 20/10; G16H 20/40; G16H 50/70; G16H 10/65; G16H 30/40; G16H 70/60; A62B 18/08; A62B 18/02; G06T 2207/30201; G06T 7/74; G06T 2207/30048; G06T 2207/30061; G06T 7/254

See application file for complete search history.

(56) References Cited

U.S. PATENT DOCUMENTS

| | | | |
|---|---|---|---|
| 5,740,267 A | 4/1998 | Echerer et al. | |
| 6,310,967 B1 | 10/2001 | Heine et al. | |
| 6,532,959 B1 | 3/2003 | Berthon-Jones | |
| 6,728,589 B1 | 4/2004 | Delache et al. | |
| 7,130,453 B2 | 10/2006 | Kondo et al. | |
| 7,397,932 B2 | 7/2008 | McAlpine et al. | |
| 7,672,973 B2 | 3/2010 | Lordo | |
| 7,827,038 B2 | 11/2010 | Richard et al. | |
| 7,904,193 B2 | 3/2011 | Janbakhsh | |
| 7,916,971 B2 | 3/2011 | Bigioi et al. | |
| 8,254,637 B2 | 8/2012 | Abourizk et al. | |
| 8,634,900 B2 | 1/2014 | Smith | |
| 8,861,783 B1 | 10/2014 | Peleg | |
| 8,879,813 B1 | 11/2014 | Solanki et al. | |
| 9,177,130 B2 | 11/2015 | Nechyba et al. | |
| 10,220,172 B2 | 3/2019 | Lucey et al. | |
| 2002/0059257 A1 | 5/2002 | Matsumura et al. | |
| 2002/0093515 A1 | 7/2002 | Fay et al. | |
| 2002/0161664 A1 | 10/2002 | Shaya et al. | |
| 2003/0090625 A1 | 5/2003 | Izumitani | |
| 2005/0089213 A1 | 4/2005 | Geng | |
| 2006/0023228 A1 | 2/2006 | Geng | |
| 2006/0235877 A1 | 10/2006 | Richard et al. | |
| 2008/0060652 A1 | 3/2008 | Selvarajan et al. | |
| 2008/0078396 A1* | 4/2008 | Janbakhsh ............ | A61M 16/06 128/205.25 |
| 2008/0118143 A1 | 5/2008 | Gordon et al. | |
| 2008/0317314 A1 | 12/2008 | Schwartz et al. | |
| 2009/0044808 A1 | 2/2009 | Guney et al. | |
| 2010/0000534 A1 | 1/2010 | Kooij et al. | |
| 2010/0007726 A1 | 1/2010 | Barbieri et al. | |
| 2010/0061601 A1 | 3/2010 | Abramoff et al. | |
| 2010/0172567 A1 | 7/2010 | Prokoski | |
| 2011/0299754 A1 | 12/2011 | Suri | |
| 2012/0075168 A1* | 3/2012 | Osterhout ............... | G06F 3/017 345/8 |
| 2012/0245962 A1 | 9/2012 | Smith et al. | |
| 2012/0279507 A1 | 11/2012 | Duke | |
| 2012/0287163 A1 | 11/2012 | Djavaherian | |
| 2012/0305003 A1 | 12/2012 | Mark | |
| 2013/0109915 A1 | 5/2013 | Krupnik et al. | |
| 2014/0052681 A1 | 2/2014 | Nitz et al. | |
| 2014/0152792 A1 | 6/2014 | Krueger | |
| 2014/0152859 A1 | 6/2014 | Chen | |
| 2014/0250523 A1 | 9/2014 | Savvides et al. | |
| 2014/0261430 A1 | 9/2014 | Davis | |
| 2014/0278319 A1 | 9/2014 | Thiruvengada et al. | |
| 2014/0278320 A1* | 9/2014 | Wang ..................... | G06F 30/20 703/11 |
| 2014/0278552 A1 | 9/2014 | Hold | |
| 2014/0288463 A1 | 9/2014 | De Waele et al. | |
| 2014/0341442 A1 | 11/2014 | Lewis et al. | |
| 2014/0352134 A1 | 12/2014 | Ho | |
| 2014/0354830 A1 | 12/2014 | Schafer et al. | |
| 2015/0055140 A1 | 2/2015 | Deguilio | |
| 2015/0065803 A1 | 3/2015 | Douglas et al. | |
| 2015/0306330 A1 | 10/2015 | Richard | |
| 2016/0004820 A1* | 1/2016 | Moore ................... | G16H 15/00 705/3 |
| 2016/0097716 A1 | 4/2016 | Gulati et al. | |

FOREIGN PATENT DOCUMENTS

| | | |
|---|---|---|
| CN | 101529446 A | 9/2009 |
| CN | 101534698 A | 9/2009 |
| CN | 101652097 A | 2/2010 |
| CN | 102668541 A | 9/2012 |
| CN | 102821808 A | 12/2012 |
| CN | 103024338 A | 4/2013 |
| CN | 103324909 A | 9/2013 |
| CN | 104471589 A | 3/2015 |
| CN | 104704531 A | 6/2015 |
| DE | 10000790 A1 | 7/2001 |
| WO | 1998004310 A1 | 2/1998 |
| WO | 2004073778 A1 | 9/2004 |
| WO | 2005063328 A1 | 7/2005 |
| WO | 2006074513 A1 | 7/2006 |
| WO | 2006130903 A1 | 12/2006 |
| WO | 2009001512 A1 | 12/2008 |
| WO | 2009052560 A1 | 4/2009 |
| WO | 2010135785 A1 | 12/2010 |
| WO | 2014009914 A2 | 1/2014 |
| WO | 2014053010 A1 | 4/2014 |
| WO | 2014057392 A1 | 4/2014 |
| WO | 2014097060 A2 | 6/2014 |
| WO | 2014180657 A2 | 11/2014 |
| WO | 2014180671 A2 | 11/2014 |
| WO | 2014180739 A1 | 11/2014 |
| WO | 2014180944 A1 | 11/2014 |

OTHER PUBLICATIONS

"Canon EOS 60 digital SLR photography from entry to master" digital creativity, pp. 17-19, Anhui Science and Technology Press, Feb. 28, 2015.

IOT security, Liu Jianhua, p. 117, China Railway Press, Sep. 30, 2013.

Chinese Office Action dated Sep. 8, 2020 for CN Patent Application No. 2016800388955.

Extended EP Search Report issued in corresponding EP application No. 16 81 6861.5 dated Feb. 12, 2019.

International Search Report to PCT/AU2016/050560.

(56) References Cited

OTHER PUBLICATIONS

""""The LenSx Laser System SoftFit(TM) Patient Interface I myalcon. com"""", Apr. 30, 2015 (Apr. 30, 2015), XP055551191, Retrieved from the Internet: URL:https://web.archive.org/web/20150430195720/ https:// www.myalcon.com/products/surgical/lensx-laser/softfit. shtml [retrieved on Feb. 4, 2019].

"Server (computing)—Wikipedia", Dec. 21, 2014 (Dec. 21, 2014), XP055550980, Retrieved from the Internet: URL:https://en.wikipedia. org/w/index.php?title=Server_(computing)&oldid=639067143 [retrieved on Feb. 1, 2019].

Cootes, T. F., et al., Active Shape Models—Their Training and Application. Computer Vision and Image Understanding, 61(1), 38-59 (1995).

Rufer, Florian, et al., White-to-White Corneal Diameter: Normal Values in Healthy Humans Obtained With the Orbscan II Topography System. Cornea, 24(3), 259-261, Apr. 2005.

West, John B, "Respiratory Physiology", Lippincott Williams & Wilkins, 9th edition published 2011.

European Office Action for Application No. EP16816861.5 dated Mar. 23, 2022.

Fenlon, Riley, "Facial Respirator Shape Analysis using 3D Anthropometric Data", NIST, 2007, pp. 2-18.

Godil, Afzal, "Facial Shape Analysis and Sizing System", National Institute of Standards and Technology, Digital Human Modeling, HCH 2009, LNCS 5620, pp. 29-35, 2009.

Office Action issued in corresponding Chinese Patent Application No. 202111205800.3, dated Oct. 19, 2023, 6 pages.

\* cited by examiner

MASK SIZING TOOL USING A MOBILE APPLICATION

1 CROSS-REFERENCE TO RELATED APPLICATIONS

This application is a continuation of U.S. patent application Ser. No. 15/578,440, filed Nov. 30, 2017, which is a national phase entry under 35 U.S.C. § 371 of International Application No. PCT/AU2016/050560, filed Jun. 30, 2016, published in English, which claims priority from U.S. Provisional Patent Application Nos. 62/313,202, filed Mar. 25, 2016 and 62/186,461, filed Jun. 30 2015, all of which are incorporated herein by reference.

2 STATEMENT REGARDING FEDERALLY SPONSORED RESEARCH OR DEVELOPMENT

Not Applicable

3 THE NAMES OF PARTIES TO A JOINT RESEARCH DEVELOPMENT

Not Applicable

4 SEQUENCE LISTING

Not Applicable

5 BACKGROUND OF THE TECHNOLOGY

5.1 Field of the Technology

The present technology relates to one or more of the detection, diagnosis, treatment, prevention and amelioration of respiratory-related disorders. The present technology also relates to medical devices or apparatus, and their use.

5.2 Description of the Related Art

5.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising.

5.2.2 Positive Pressure Therapies

Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient in taking a full breath and/or maintain adequate oxygen levels in the body by doing some or all of the work of breathing. The ventilatory support is provided via a patient interface. NIV has been used to treat CSR, OHS, COPD, MD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

5.2.3 Diagnosis and Treatment Systems

These therapies may be provided by a treatment system or device. Systems and devices may also be used to diagnose a condition without treating it.

A treatment system may comprise a Respiratory Pressure Therapy Device (RPT device), an air circuit, a humidifier, a patient interface, and data management.

Another form of treatment system is a mandibular repositioning device.

5.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. For example, masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

5.2.3.1.1 Seal-Forming Portion

Patient interfaces may include a seal-forming portion. Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming portion that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming portions may be designed for mass manufacture such that one design fit and be comfortable and effective for a wide range of different face shapes and sizes. To the extent to which there is a mismatch between the shape of the patient's face, and the seal-forming portion of the mass-manufactured patient interface, one or both must adapt in order for a seal to form.

One type of seal-forming portion extends around the periphery of the patient interface, and is intended to seal against the patient's face when force is applied to the patient interface with the seal-forming portion in confronting engagement with the patient's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming portion does not match that of the patient, it may crease or buckle in use, giving rise to leaks.

Another type of seal-forming portion may comprise a friction-fit element, e.g. for insertion into a naris, however some patients find these uncomfortable.

Another form of seal-forming portion may use adhesive to achieve a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

5.2.3.1.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

5.2.3.1.3 Patient Interface Sizing

Patient interfaces, as described above, may be provided to a patient in various forms, such as a nasal mask or full-face mask/oro-nasal mask (FFM) or nasal pillows mask, for example. Such patient interfaces are manufactured with various dimensions to accommodate a specific patient's anatomical features in order to facilitate a comfortable interface that is functional to provide, for example, positive pressure therapy. Such patient interface dimensions may be customized to correspond with a particular patient's specific facial anatomy or may be designed to accommodate a population of individuals that have an anatomy that falls within predefined spatial boundaries or ranges. However in some cases masks may come in a variety of standard sizes from which a suitable one must be chosen.

In this regard, sizing a patient interface for a patient is typically performed by a trained individual, such as a Durable Medical Equipment (DME) provider or physician. Typically a patient needing a patient interface to begin or continue positive pressure therapy would visit the trained individual at an accommodating facility where a series of measurements are made in an effort to determine an appropriate patient interface size from standard sizes. An appropriate size is intended to mean a particular combination of dimensions of certain features, such as the seal forming structure, of a patient interface, which provide adequate comfort and sealing to effectuate positive pressure therapy. Sizing in this way is not only labor intensive but also inconvenient. The inconvenience of taking time out of a busy schedule or, in some instances, having to travel great distances is a barrier to many patients receiving a new or replacement patient interface and ultimately a barrier to receiving treatment. Nevertheless, selection of the most appropriate size is important for treatment quality and compliance.

6 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance of patients with respiratory therapy.

One form of the present technology comprises automatic sizing of a patient interface without the assistance of a trained individual.

Another aspect of one form of the present technology is the automatic measurement of a patient's facial features based on data collected from the patient.

Another aspect of one form of the present technology is the automatic recommendation of a patient interface size based on a comparison between data collected from a patient to a corresponding data record.

Another aspect of one form of the present technology is a mobile application that conveniently determines an appropriate patient interface size for a particular patient based on a two-dimensional image.

Some versions of the present technology include automated method(s) for selecting a patient interface according to patient interface size. The method(s) may operate in one or more processors. The method may include receiving image data captured by an image sensor. The captured image data may contain one or more facial features of an intended user of the patient interface in association with a predetermined reference feature having a known dimension. The method may include detecting one or more facial features of the user in the captured image data. The method may include detecting the predetermined reference feature in the captured image data. The method may include processing image pixel data of the image to measure an aspect of the one or more facial features detected in the image based on the predetermined reference feature. The method may include selecting a patient interface size from a group of standard patient interface sizes based on a comparison between the measured aspect of the one or more facial features and a data record relating sizing information of the group of standard patient interface sizes and the measured aspect of the one or more facial features.

In some versions, the aspect of the one or more facial features may include a distance between a sellion and supramenton of the user. The method may include calculating a value of the measured aspect based on a scaling factor derived from the reference feature. The method may include adjusting a value of the measured aspect with an anthropometric correction factor. The anthropometric correction factor may be calculated based on patient interface return data. The method may include calculating the scaling factor as a function of the known dimension of the predetermined reference feature and a detected pixel count for the detected reference feature. The predetermined reference feature may be a coin. The detecting the reference feature may include applying a cascade classifier to the captured image data. The method may include calculating a value of the measured aspect based on a scaling factor derived from the coin. The method may include calculating the scaling factor as a function of the known dimension of the coin in the captured image data and a detected pixel count for the coin that is detected. The detected pixel count for the coin that is detected may be a width of an ellipse fitted to the coin. The predetermined reference feature may be a cornea of the user.

In some versions, the method may include, for image capture, displaying the reference feature on a display interface of a display device coupled with the image sensor. The display interface may include a targeting guide and a live action preview of content detected by the image sensor. The content may include the reference feature as displayed on the display interface. The method may include controlling capturing of the image data to satisfy at least one alignment condition. The at least one alignment condition may include detection of positioning of the reference feature of the live action preview within a box of the targeting guide. The at least one alignment condition may include detection of a tilt condition being within about +/−10 degrees of a superior-inferior extending axis. The at least one alignment condition may include detection of a tilt condition being within about +/−5 degrees of a superior-inferior extending axis. Detection of a tilt condition may be performed by reading an inertial measurement unit (IMU).

In some versions, the predetermined reference feature may be a QR code. The patient interface may include a mask. The patient interface may include a nasal mask. Optionally, the processing image pixel data may include counting pixels. The method may include generating an automated electronic offer for a patient interface for purchase based on the selected patient interface size. The method may include calculating an average of the measured aspect of the facial feature from a plurality of captured images of the one or more facial features.

Some versions of the present technology include a system(s) for automatically recommending a patient interface size complementary to a particular patient's facial features. The system(s) may include one or more servers. The one or more servers may be configured to communicate with a computing device over a network. The one or more servers may be configured to receive image data captured by an image sensor, where the captured image data may contain one or more facial features of an intended user of the patient interface in association with a predetermined reference feature having a known dimension. The one or more servers may be configured to detect one or more facial features of the user in the captured image data. The one or more servers may be configured to detect the predetermined reference feature in the captured image data. The one or more servers may be configured to process image pixel data of the image to measure an aspect of the one or more facial features detected in the image based on the predetermined reference feature. The one or more servers may be configured to select a patient interface size from a group of standard patient interface sizes based on a comparison between the measured aspect of the one or more facial features and a data record relating sizing information of the group of standard patient interface sizes and the measured aspect of the one or more facial features.

In some versions, the aspect of the one or more facial features may include a distance between a sellion and supramenton of the user. The one or more servers may be configured to calculate a value of the measured aspect based on a scaling factor derived from the reference feature. The one or more servers may be configured to adjust a value of the measured aspect with an anthropometric correction factor. The anthropometric correction factor may be calculated based on patient interface return data. The one or more servers may be configured to calculate the scaling factor as a function of the known dimension of the predetermined reference feature and a detected pixel count for the detected reference feature. The predetermined reference feature may include a coin. The one or more servers may be configured to detect the reference feature by applying a cascade classifier to the captured image data. The one or more servers may be further configured to calculate a value of the measured aspect based on a scaling factor derived from the coin. The one or more servers may be configured to calculate the scaling factor as a function of the known dimension of the coin in the captured image data and a detected pixel count for the coin that is detected. The detected pixel count for the coin that is detected may be a width of an ellipse fitted to the coin. The predetermined reference feature may be a cornea of the user.

In some versions, the system may include the computing device. The computing devices may be configured to, for image capture, generate a display of the reference feature on a display interface of a display device that may be coupled with the image sensor. The display interface may include a targeting guide and a live action preview of content detected by the image sensor. The content may include the reference feature as displayed on the display interface. The computing device may be further configured to control capturing of the image data to satisfy at least one alignment condition. The at least one alignment condition may include detection of positioning of the reference feature of the live action preview within a box of the targeting guide. The at least one alignment condition may include detection of a tilt condition being within about +/−10 degrees of a superior-inferior extending axis. The at least one alignment condition may include detection of a tilt condition being within about +/−5 degrees of a superior-inferior extending axis. The detection of a tilt condition may be performed by reading an inertial measurement unit (IMU).

In some versions, the predetermined reference feature may include a QR code. The patient interface may include a mask. The patient interface may include a nasal mask. In some cases, to process image pixel data, the one or more servers may be configured to count pixels. The one or more servers may be configured to generate an automated electronic offer for a patient interface for purchase based on the selected patient interface size. The one or more servers may be configured to calculate an average of the measured aspect of the facial feature from a plurality of captured images of the facial features. The one or more servers may be configured to communicate the selected patient interface size to the computing device over the network.

Some versions of the present technology include a system(s) for automatically recommending a patient interface size complementary to a particular patient's facial features. The system(s) may include a mobile computing device. The mobile computing device may be configured to communicate with one or more servers over a network. The mobile computing device may be configured to receive captured image data of an image. The captured image data may contain one or more facial features of a user in association with a predetermined reference feature having a known dimension. The image data may be captured with an image sensor. The mobile computing device may be configured to detect one or more facial features of the user in the captured image data. The mobile computing device may be configured to detect the predetermined reference feature in the captured image data. The mobile computing device may be configured to process image pixel data of the image to measure an aspect of the one or more facial features detected in the image based on the predetermined reference feature. The mobile computing device may be configured to select a patient interface size from a group of standard patient interface sizes based on a comparison between the measured aspect of the one or more facial features and a data record relating sizing information of the group of standard patient interface sizes and the measured aspect of the one or more facial features.

In some versions, the aspect of the one or more facial features may include a distance between a sellion and supramenton of the user. The mobile computing device may be configured to calculate a value of the measured aspect based on a scaling factor derived from the reference feature. The mobile computing device may be further configured to adjust a value of the measured aspect with an anthropometric correction factor. The anthropometric correction factor may be calculated based on patient interface return data. The mobile computing device may be configured to calculate the scaling factor as a function of the known dimension of the predetermined reference feature and a detected pixel count for the detected reference feature. The predetermined reference feature may be a coin. The mobile computing device may be configured to detect the reference feature by applying a cascade classifier to the captured image data. The mobile computing device may be configured to calculate a value of the measured aspect based on a scaling factor derived from the coin. The mobile computing device may be configured to calculate the scaling factor as a function of the known dimension of the coin in the captured image data and a detected pixel count for the coin that is detected. The detected pixel count for the coin that is detected may be a width of an ellipse fitted to the coin. In some versions, the predetermined reference feature may be a cornea of the user. T The mobile computing device may be configured to, for the image capture, generate a display of the reference feature on a display interface of a display device that may be coupled with the image sensor. The display interface may include a targeting guide and a live action preview of content detected by the image sensor. The content may include the reference feature as displayed on the display interface. The mobile computing device may be configured to control capturing of the image data to satisfy at least one alignment condition. The at least one alignment condition may include detection of positioning of the reference feature of the live action preview within a box of the targeting guide. The at least one alignment condition may include detection of a tilt condition being within about +/−10 degrees of a superior-inferior extending axis. The at least one alignment condition may include detection of a tilt condition being within about +/−5 degrees of a superior-inferior extending axis. Detection of a tilt condition may be performed by reading an inertial measurement unit (IMU).

In some versions, the predetermined reference feature may be a QR code. The patient interface may be a mask. The patient interface may be a nasal mask. In some cases, to process image pixel data, the mobile computing device may be configured to count pixels. The mobile computing device may be configured to request an automated electronic offer for a patient interface for purchase based on the selected patient interface size. The mobile computing device may be configured to calculate an average of the measured aspect of the facial feature from a plurality of captured images of the facial features. The mobile computing device may be configured to communicate the selected patient interface size to a server over the network.

Some versions of the present technology include apparatus for automatically recommending a patient interface size complementary to a particular patient's facial features. The apparatus may include means for receiving image data captured by an image sensor. The captured image data may contain one or more facial features of an intended user of the patient interface in association with a predetermined reference feature having a known dimension. The apparatus may include means for detecting one or more facial features of the user in the captured image data. The apparatus may include means for detecting the predetermined reference feature in the captured image data. The apparatus may include means for processing image pixel data of the image to measure an aspect of the one or more facial features detected in the image based on the predetermined reference feature. The apparatus may include means for selecting a patient interface size from a group of standard patient interface sizes based on a comparison between the measured aspect of the one or more facial features and a data record relating sizing information of the group of standard patient interface sizes and the measured aspect of the one or more facial features.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

7 BRIEF DESCRIPTION OF THE DRAWINGS

The present technology is illustrated by way of example, and not by way of limitation, in the figures of the accompanying drawings, in which like reference numerals refer to similar elements including:

7.1 Treatment Systems

8 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

8.1 Treatment Systems

In one form, the present technology comprises an apparatus or device for treating a respiratory disorder. The apparatus or device may comprise an RPT device 40 for supplying pressurised air to the patient 10 via an air circuit 50 to a patient interface 100.

Figure 1A:
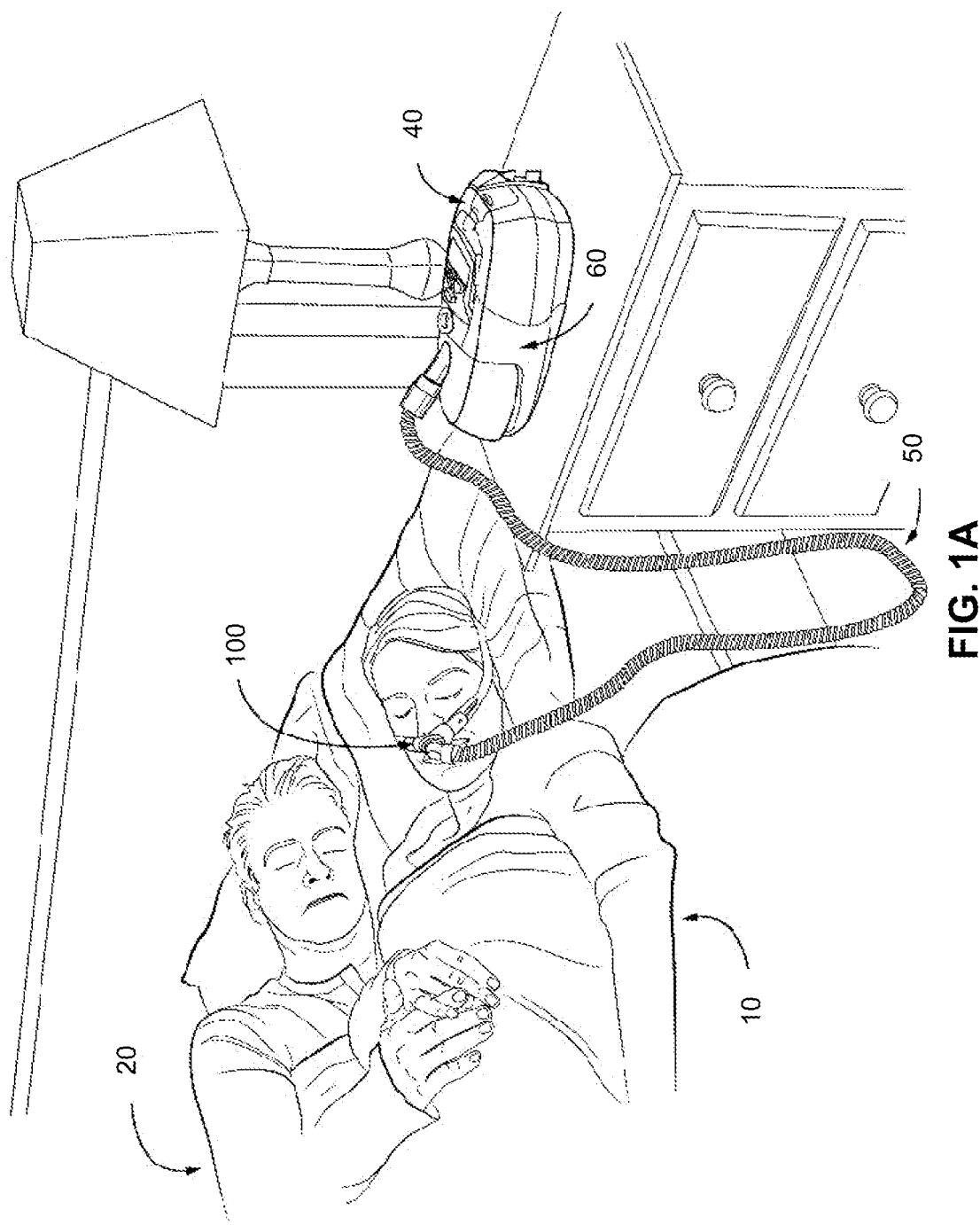
FIG. 1A shows a system including a patient wearing a patient interface in the form of a nasal pillow.

FIG. 1A shows a system including a patient 10 wearing a patient interface 100, in the form of nasal pillows, receives a supply of air at positive pressure from a RPT device 40. Air from the RPT device is humidified in a humidifier 60, and passes along an air circuit 50 to the patient 10. A bed partner 20 is also shown.

Figure 1B:
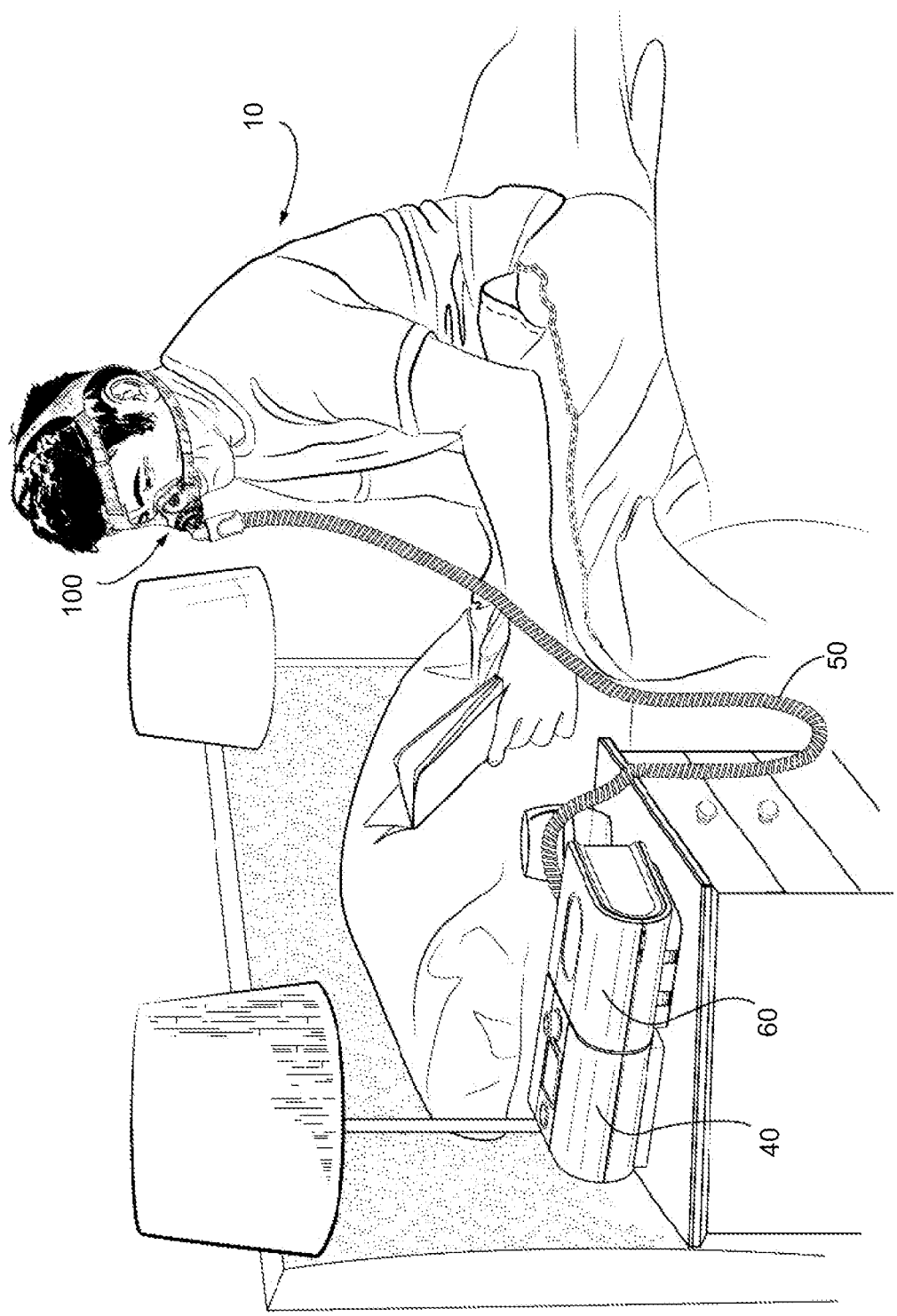
FIG. 1B shows a system including a patient wearing a patient interface in the form of a nasal mask.

FIG. 1B shows a system including a patient 10 wearing a patient interface 100, in the form of a nasal mask, receives supply air at positive pressure from an RPT device 40. Air from the RPT device is humidified in a humidifier 60, and passes along an air circuit 50 to the patient 10.

Figure 1C:
FIG. 1C shows a system including a patient wearing a patient interface in the form of a full-face mask.

FIG. 1C shows a system including a patient 10 wearing a patient interface 100, in the form of a full-face mask (FFM), receives a supply of air at positive pressure from a RPT device 40. Air from the RPT device is humidified in a humidifier 60, and passes along an air circuit 50 to the patient 10.

8.2 Patient Interface

Figure 2:
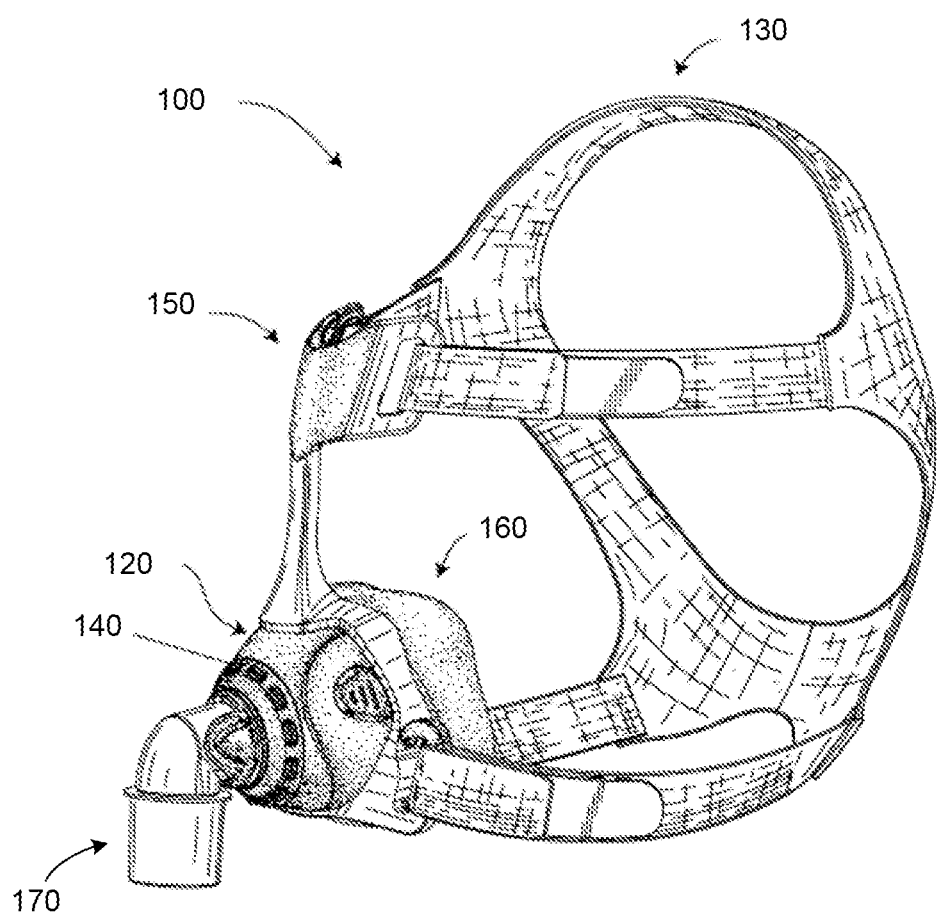
FIG. 2 shows a patient interface in the form of a nasal mask with headgear in accordance with one form of the present technology.

FIG. 2 depicts a patient interface 100 in accordance with one aspect of the present technology comprises the following functional aspects: a seal-forming structure 160, a plenum chamber 120, a positioning and stabilising structure 130, a vent 140, a forehead support 150, one form of connection port 170 for connection to air circuit 50. In some forms a functional aspect may be provided by one or more physical components. In some forms, one physical component may provide one or more functional aspects. In use the seal-forming structure 160 is arranged to surround an entrance to the airways of the patient so as to facilitate the supply of air at positive pressure to the airways.

8.2.1 Seal-Forming Structure

In one form of the present technology, a seal-forming structure 160 provides a seal-forming surface, and may additionally provide a cushioning function.

A seal-forming structure 160 in accordance with the present technology may be constructed from a soft, flexible, resilient material such as silicone.

In one form the seal-forming portion of the non-invasive patient interface 100 comprises a pair of nasal puffs, or nasal pillows, each nasal puff or nasal pillow being constructed and arranged to form a seal with a respective naris of the nose of a patient.

Nasal pillows in accordance the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

In one form, the non-invasive patient interface 100 comprises a seal-forming portion that forms a seal in use on an upper lip region (that is, the lip superior) of the patient's face.

In one form the non-invasive patient interface 100 comprises a seal-forming portion that forms a seal in use on a chin-region of the patient's face.

8.2.2 Plenum Chamber

Preferably the plenum chamber 120 has a perimeter that is shaped to be complementary to the surface contour of the face of an average person in the region where a seal will form in use. In use, a marginal edge of the plenum chamber 120 is positioned in close proximity to an adjacent surface of the face. Actual contact with the face is provided by the seal-forming structure 160. The seal-forming structure 160 may extend in use about the entire perimeter of the plenum chamber 120.

8.2.3 Positioning and Stabilising Structure

Preferably the seal-forming structure 160 of the patient interface 100 of the present technology may be held in sealing position in use by the positioning and stabilising structure 130.

8.2.4 Vent

In one form, the patient interface 100 includes a vent 140 constructed and arranged to allow for the washout of exhaled carbon dioxide.

One form of vent 140 in accordance with the present technology comprises a plurality of holes, for example, about 20 to about 80 holes, or about 40 to about 60 holes, or about 45 to about 55 holes.

8.2.5 Terms Used in Relation to a Patient Interface

Plenum chamber: a mask plenum chamber will be taken to mean a portion of a patient interface having walls enclosing a volume of space, the volume having air therein pressurised above atmospheric pressure in use. A shell may form part of the walls of a mask plenum chamber.

Seal: The noun form ("a seal") will be taken to mean a structure or barrier that intentionally resists the flow of air through the interface of two surfaces. The verb form ("to seal") will be taken to mean to resist a flow of air.

8.3 Anatomy of the Face

Figure 3A:
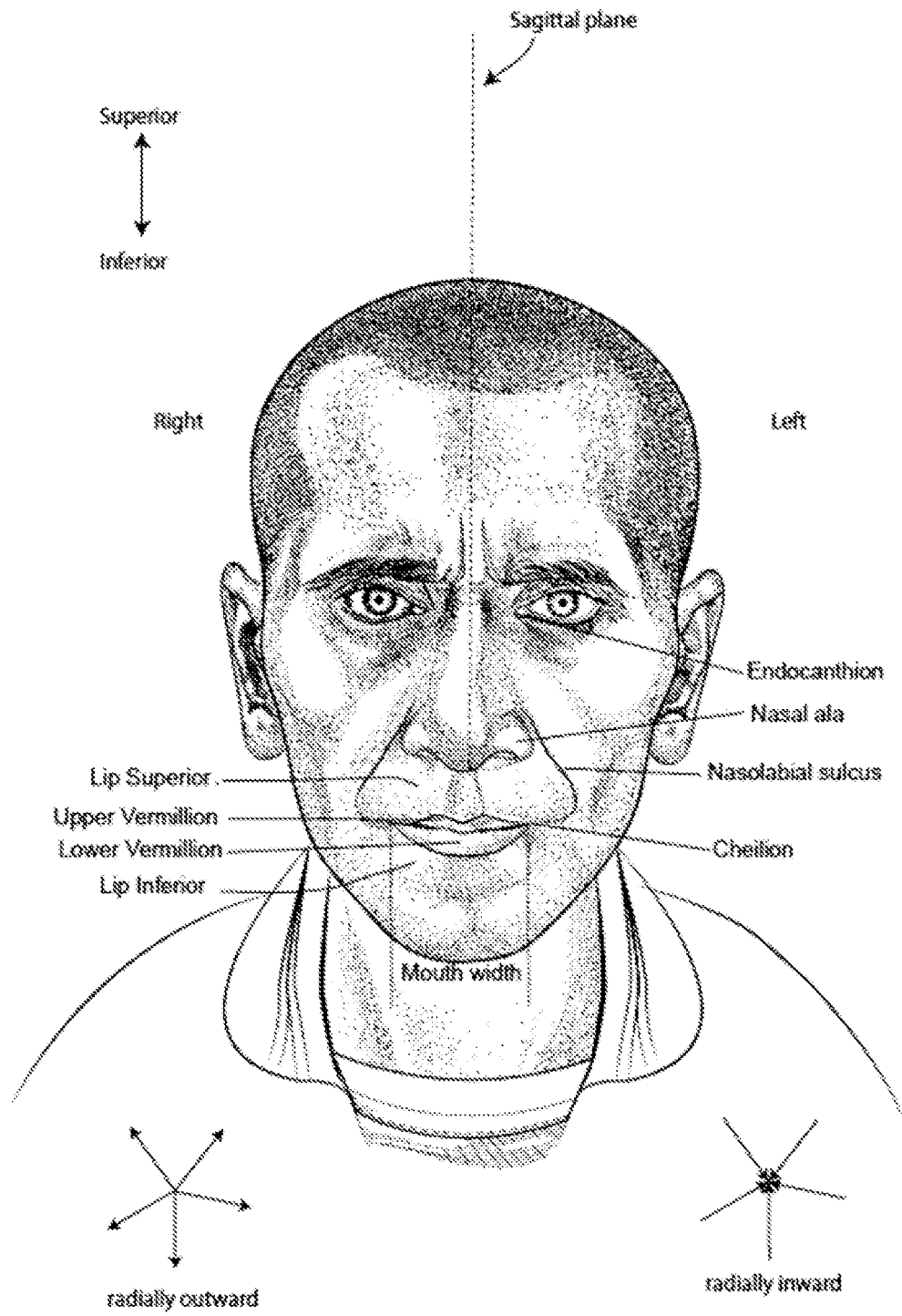
FIG. 3A is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.

FIG. 3A shows an anterior view of a human face including the endocanthion, nasal ala, nasolabial sulcus, lip superior and inferior, upper and lower vermillion, and chelion. Also shown are the mouth width, the sagittal plane dividing the head into left and right portions, and directional indicators. The directional indicators indicate radial inward/outward and superior/inferior directions.

Figure 3B:
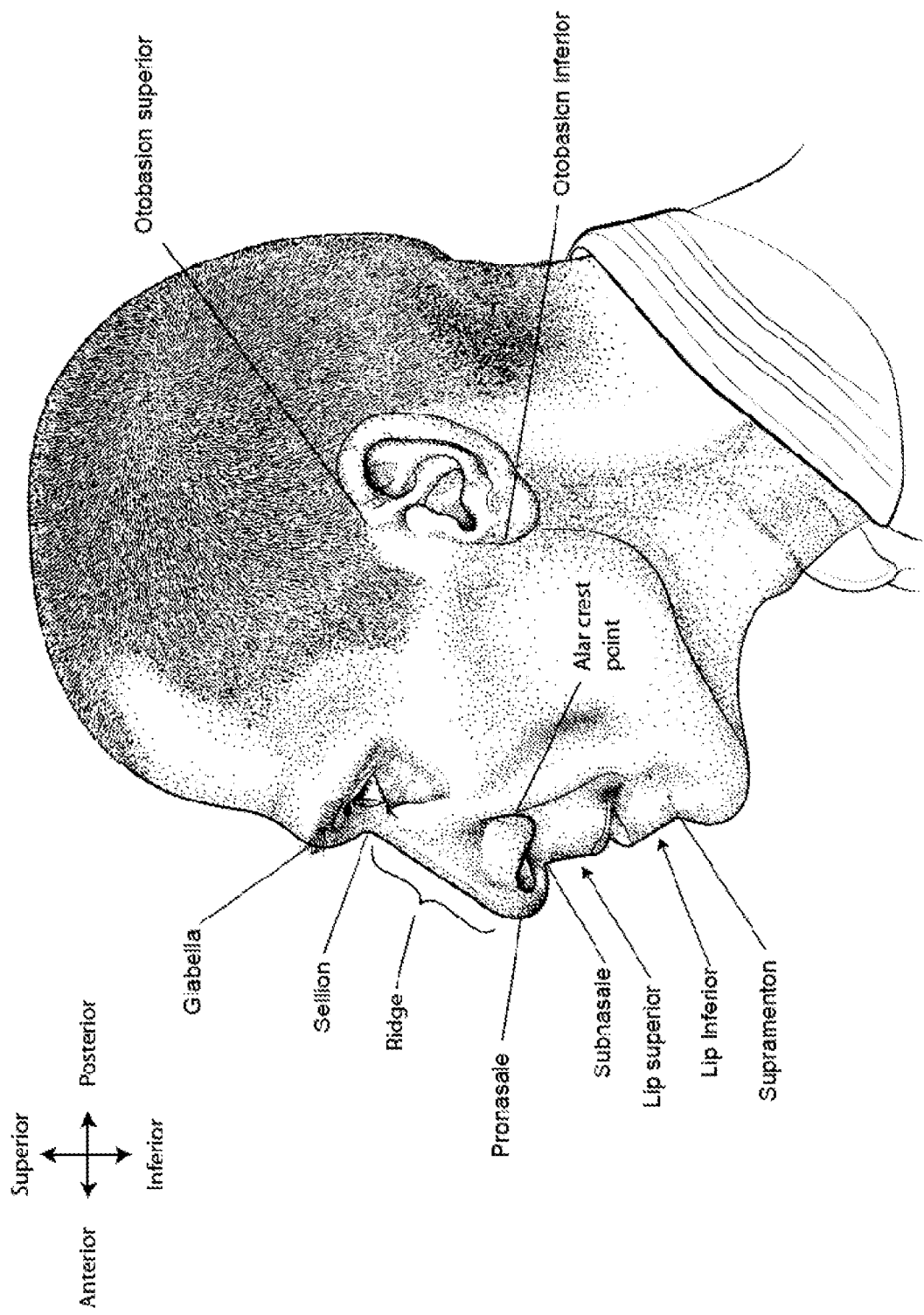
FIG. 3B is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.

FIG. 3B shows a lateral view of a human face including the glabaella, sellion, nasal ridge, pronasale, subnasale, superior and inferior lip, supramenton, alar crest point, and otobasion superior and inferior. Also shown are directional indictors indicating superior/inferior and anterior/posterior directions.

Figure 3C:
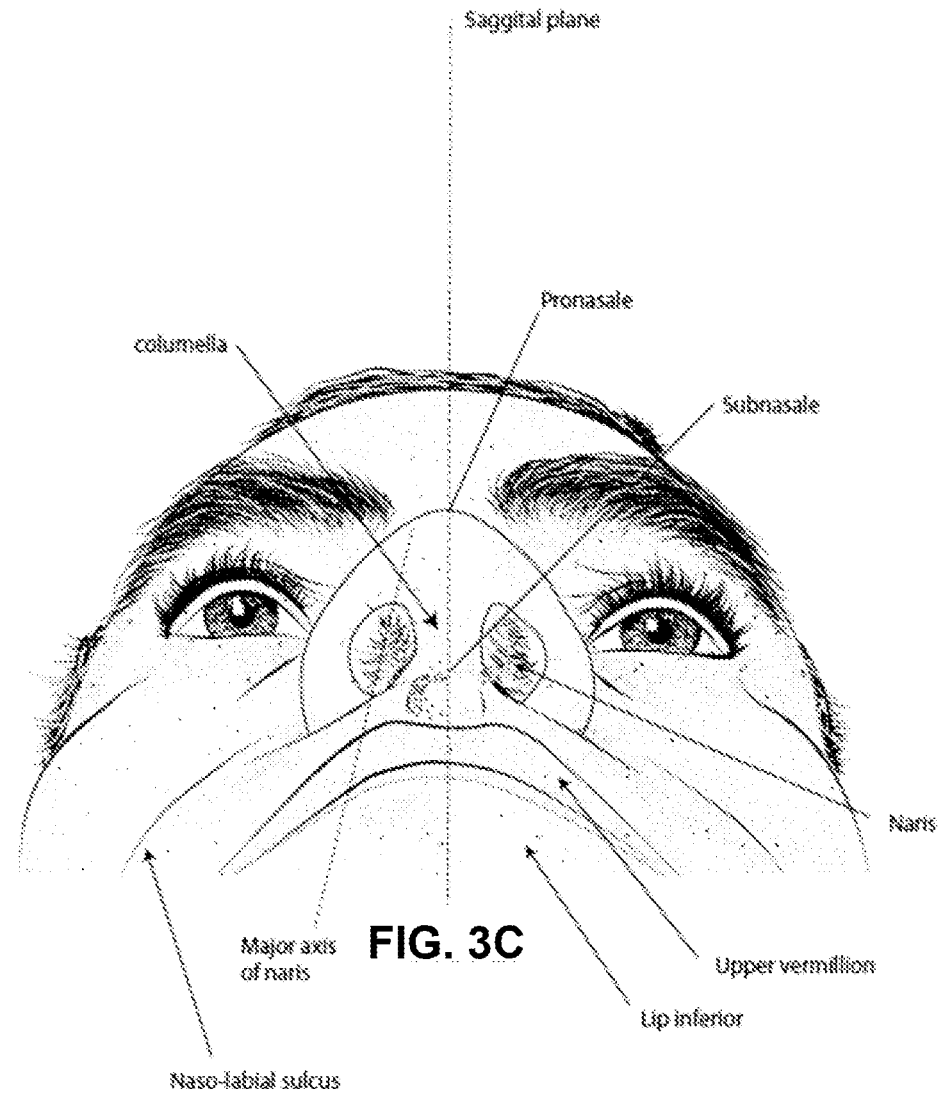
FIG. 3C is a base view of a nose with several features identified including naso-labial sulcus, lip inferior, upper Vermilion, naris, subnasale, columella, pronasale, the major axis of a naris and the sagittal plane.

FIG. 3C shows a base view of a nose with several features identified including naso-labial sulcus, lip inferior, upper Vermilion, naris, subnasale, columella, pronasale, the major axis of a naris and the sagittal plane.

8.3.1 Terms Used in Relation to the Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

Columella: the strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

*Glabella*: Located on the soft tissue, the most prominent point in the midsagittal plane of the forehead.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion

8.4 Automatic Patient Interface Sizing

8.4.1 Overview

Obtaining a patient interface allows a patient to engage in positive pressure therapy. Patients seeking their first patient interface or a new patient interface to replace an older interface, typically consult a DME to determine a recommended patient interface size based on measurements of the patient's facial anatomy, which are typically performed by the DME. This may be an inconvenience that prevents some patients from receiving a needed patient interface and from engaging in positive pressure therapy. The present technology allows patients to more quickly and conveniently obtain a patient interface. It may permit a more efficient method to quickly measure their facial anatomy and receive a recommendation for an appropriate patient interface size from the comfort of their own home using a computing device, such as a desktop computer, tablet, smart phone or other mobile device.

In a beneficial embodiment, the present technology may employ an application downloadable from a manufacturer or third party server to a smartphone or tablet with an integrated camera. When launched, the application may provide visual and/or audio instructions. As instructed, the user (i.e. a patient) may stand in front of a mirror 330, and press the camera button on a user interface. An activated process may then take a series of pictures of the user's face, and then, within a matter of seconds for example, recommend a patient interface size for the user (based on the processor analysing the pictures). This is a vast improvement over the traditional method of visiting a DME who takes a series of measurements with a calliper as it allows a user, anywhere in the world, to quickly and conveniently find a patient interface suitable for their needs. Thus, it can allow patients to begin treatment more rapidly. Moreover, in that the user has control over the process, the customer can repeat it if desired, unhurriedly and to their satisfaction, increasing the user's confidence and sense of responsibility.

As described further below, the present technology allows a user/patient to capture an image or series of images of their facial structure. Instructions provided by an application stored on a computer-readable medium, such as when executed by a processor, detect various facial landmarks within the images, measure and scale the distance between such landmarks, compare these distances to a data record, and recommend an appropriate patient interface size. Thus, an automated device of a consumer may permit accurate patient interface selection, such as in the home, to permit customers to determine sizing without trained associates.

8.4.2 System

Figure 4:
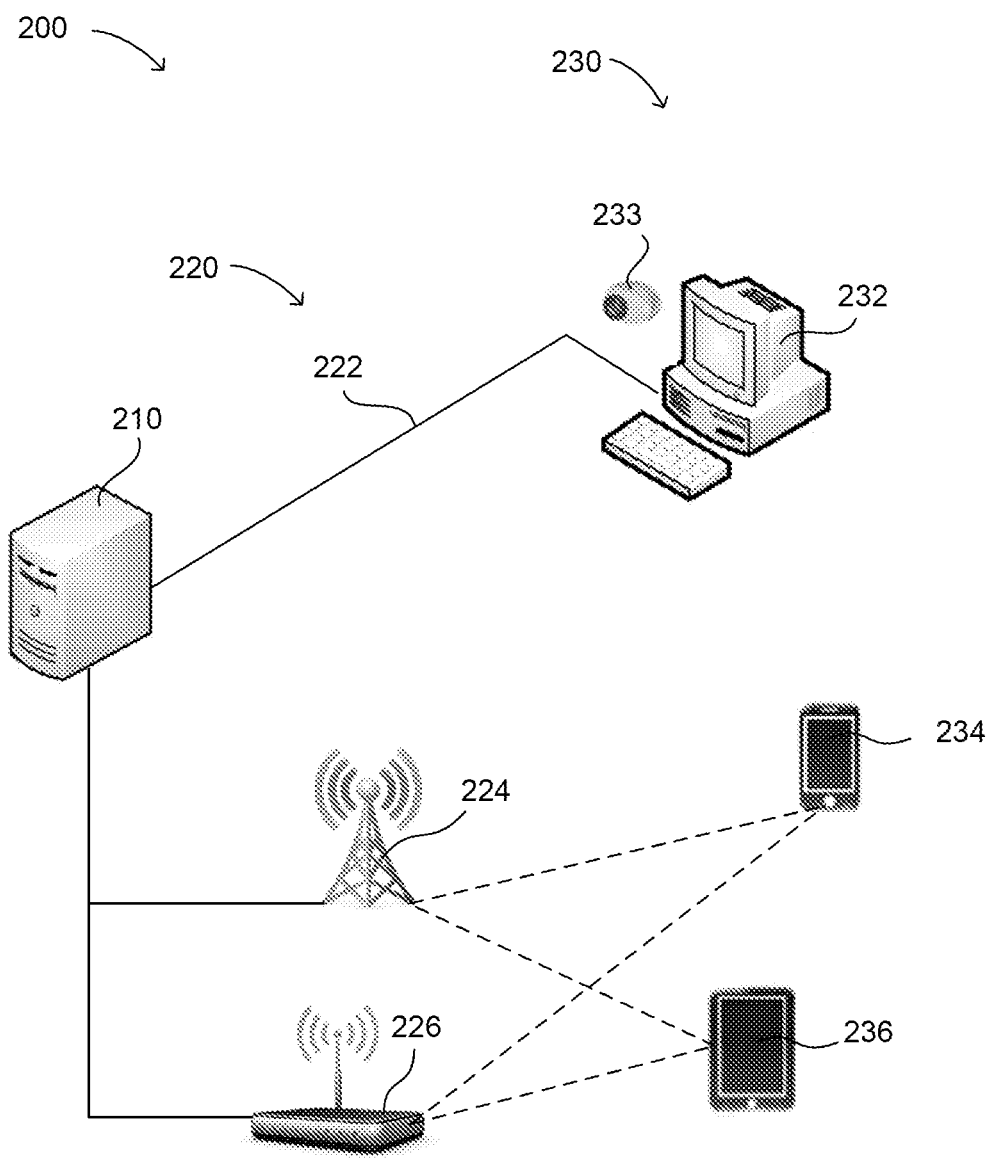
FIG. 4 is a diagram of an example system for automatically sizing a patient interface which includes a computing device.

FIG. 4 depicts an example system 200 that may be implemented for automatic facial feature measuring and patient interface sizing. System 200 may generally include one or more of servers 210, a communication network 220, and a computing device 230. Server 210 and computing device 230 may communicate via communication network 220, which may be a wired network 222, wireless network 224, or wired network with a wireless link 226. In some versions, server 210 may communicate one-way with computing device 230 by providing information to computing device 230, or vice versa. In other embodiments, server 210 and computing device 230 may share information and/or processing tasks. The system may be implemented, for example, to permit automated purchase of patient's interfaces (mask) where the process may include automatic sizing processes described in more detail herein. For example, a customer may order a mask online after running a mask selection process that automatically identifies a suitable mask size by image analysis of the customer's facial features.

8.4.2.1 Computing Device

Figure 5:
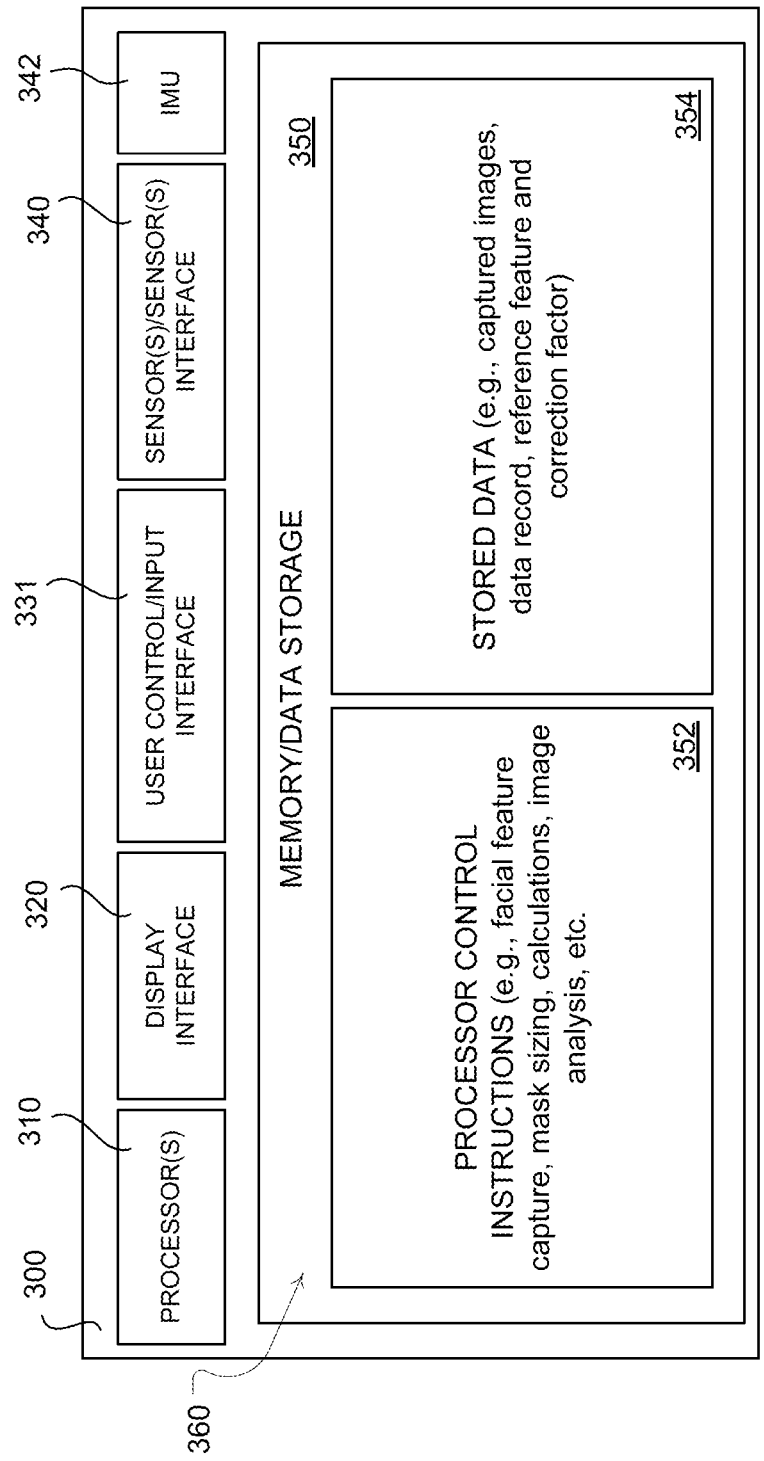
FIG. 5 is a block diagram of an example architecture of a computing device for the system of FIG. 4 including example components suitable for implementing the methodologies of the present technology.

Computing device 230 can be a desktop or laptop computer 232 or a mobile device, such as a smartphone 234 or tablet 236. FIG. 5 depicts the general architecture 300 of computing device 230. Device 230 may include one or more processors 310. Device 230 may also include a display interface 320, user control/input interface 331, sensor 340 and/or a sensor interface for one or more sensor(s), inertial measurement unit (IMU) 342 and non-volatile memory/data storage 350.

Sensor 340 may be one or more cameras (e.g., a CCD charge-coupled device or active pixel sensors) that are integrated into computing device 230, such as those provided in a smartphone or in a laptop. Alternatively, where computing device 230 is a desktop computer, device 230 may include a sensor interface for coupling with an external camera, such as the webcam 233 depicted in FIG. 4. Other exemplary sensors that could be used to assist in the methods described herein that may either be integral with or external to the computing device include stereoscopic cameras, for capturing three-dimensional images, or a light detector capable of detecting reflected light from a laser or strobing/structured light source.

User control/input interface 331 allows the user to provide commands or respond to prompts or instructions provided to the user. This could be a touch panel, keyboard, mouse, microphone, and/or speaker, for example.

Display interface 320 may include a monitor, LCD panel, or the like to display prompts, output information (such as facial measurements or interface size recommendations), and other information, such as a capture display, as described in further detail below.

Memory/data storage 350 may be the computing device's internal memory, such as RAM, flash memory or ROM. In some embodiments, memory/data storage 350 may also be an external memory linked to computing device 230, such as an SD card, server, USB flash drive or optical disc, for example. In other embodiments, memory/data storage 350 can be a combination of external and internal memory. Memory/data storage 350 includes stored data 354 and processor control instructions 352 that instruct processor 310 to perform certain tasks. Stored data 354 can include data received by sensor 340, such as a captured image, and other data that is provided as a component part of an application. Processor control instructions 352 can also be provided as a component part of an application.

8.4.2.2 Application for Facial Feature Measuring and Patient Interface Sizing

One such application is an application for facial feature measuring and/or patient interface sizing 360, which may be an application downloadable to a mobile device, such as smartphone 234 and/or tablet 236. The application 360, which may be stored on a computer-readable medium, such as memory/data storage 350, includes programmed instructions for processor 310 to perform certain tasks related to facial feature measuring and/or patient interface sizing. The application also includes data that may be processed by the algorithm of the automated methodology. Such data may include a data record, reference feature, and correction factors, as explained in additional detail below.

8.4.3 Method for Automatic Measuring and Sizing

As illustrated in the flow diagrams of FIGS. 6A-6D, one aspect of the present technology is a method for controlling a processor, such as processor 310, to measure patient facial features using two-dimensional or three-dimensional images and to recommend or select an appropriate patient interface size, such as from a group of standard sizes, based on the resultant measurements. The method may generally be characterized as including three or four different phases: a pre-capture phase 400, a capture phase 500, a post-capture image processing phase 600, and a comparison and output phase 700.

In some cases, the application for facial feature measuring and patient interface sizing may control a processor 310 to output a visual display that includes a reference feature on the display interface 320. The user may position the feature adjacent to their facial features, such as by movement of the camera. The processor may then capture and store one or more images of the facial features in association with the reference feature when certain conditions, such as alignment conditions are satisfied. This may be done with the assistance of a mirror 330. The mirror 330 reflects the displayed reference feature and the user's face to the camera. The application then controls the processor 310 to identify certain facial features within the images and measure distances therebetween. By image analysis processing a scaling factor may then be used to convert the facial feature measurements, which may be pixel counts, to standard mask measurement values based on the reference feature. Such values may be, for example, standardized unit of measure, such as a meter or an inch, and values expressed in such units suitable for mask sizing. Additional correction factors may be applied to the measurements. The facial feature measurements may be compared to data records that include measurement ranges corresponding to different patient interface sizes for particular patient interface forms, such as nasal masks and FFM's, for example. The recommended size may then be chosen and be output to the user/patient based on the comparison(s) as a recommendation. Such a process may be conveniently effected within the comfort of the user's own home, if the user so chooses. The application may perform this method within seconds. In one example, the application performs this method in real time.

8.4.3.1 Pre-Capture Phase 400

Figure 6A:
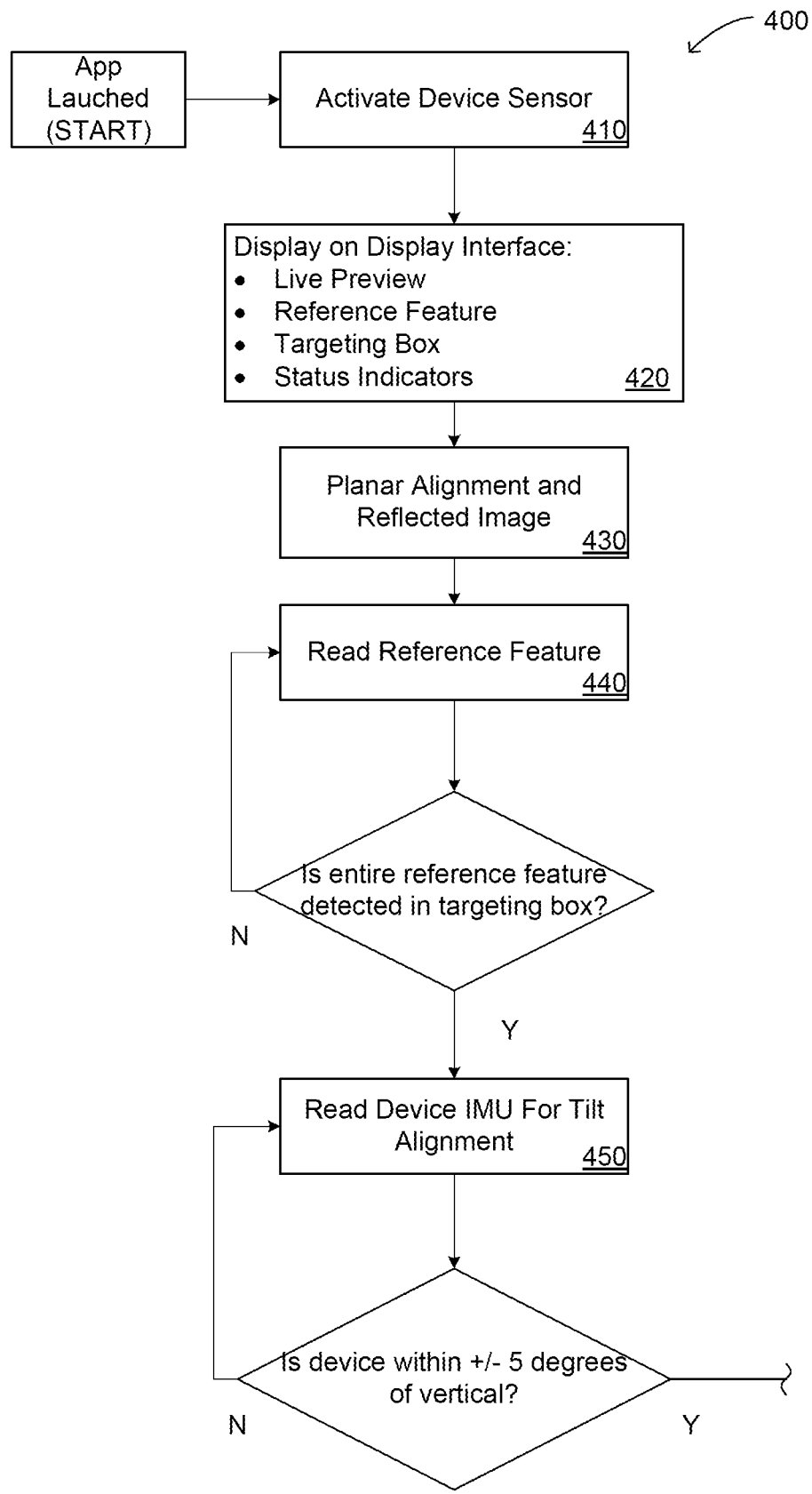
FIG. 6A is a flow diagram of a pre-capture phase method of an example version of the present technology.
Figure 6B:
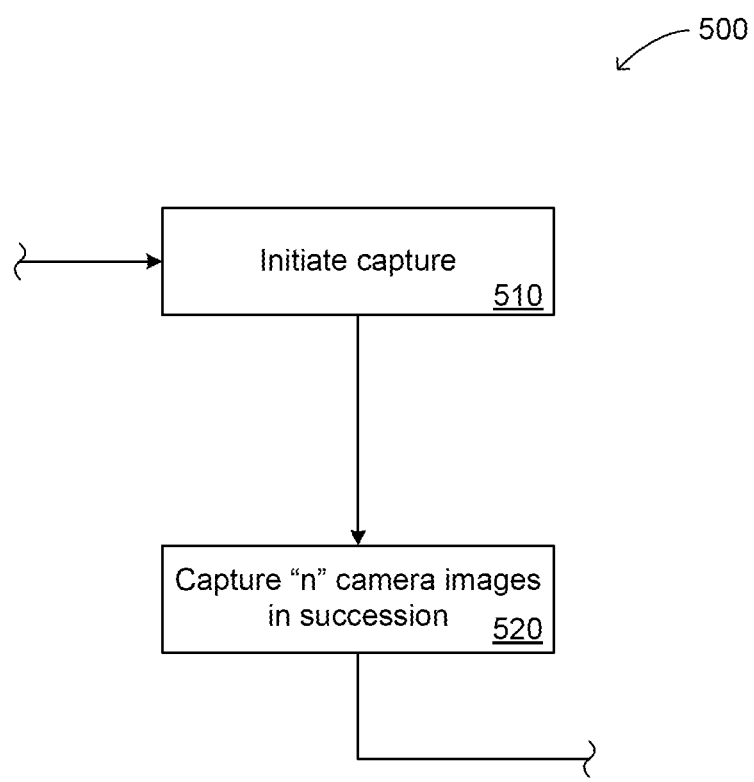
FIG. 6B is a flow diagram of a capture phase method of some versions of the present technology.
Figure 6C:
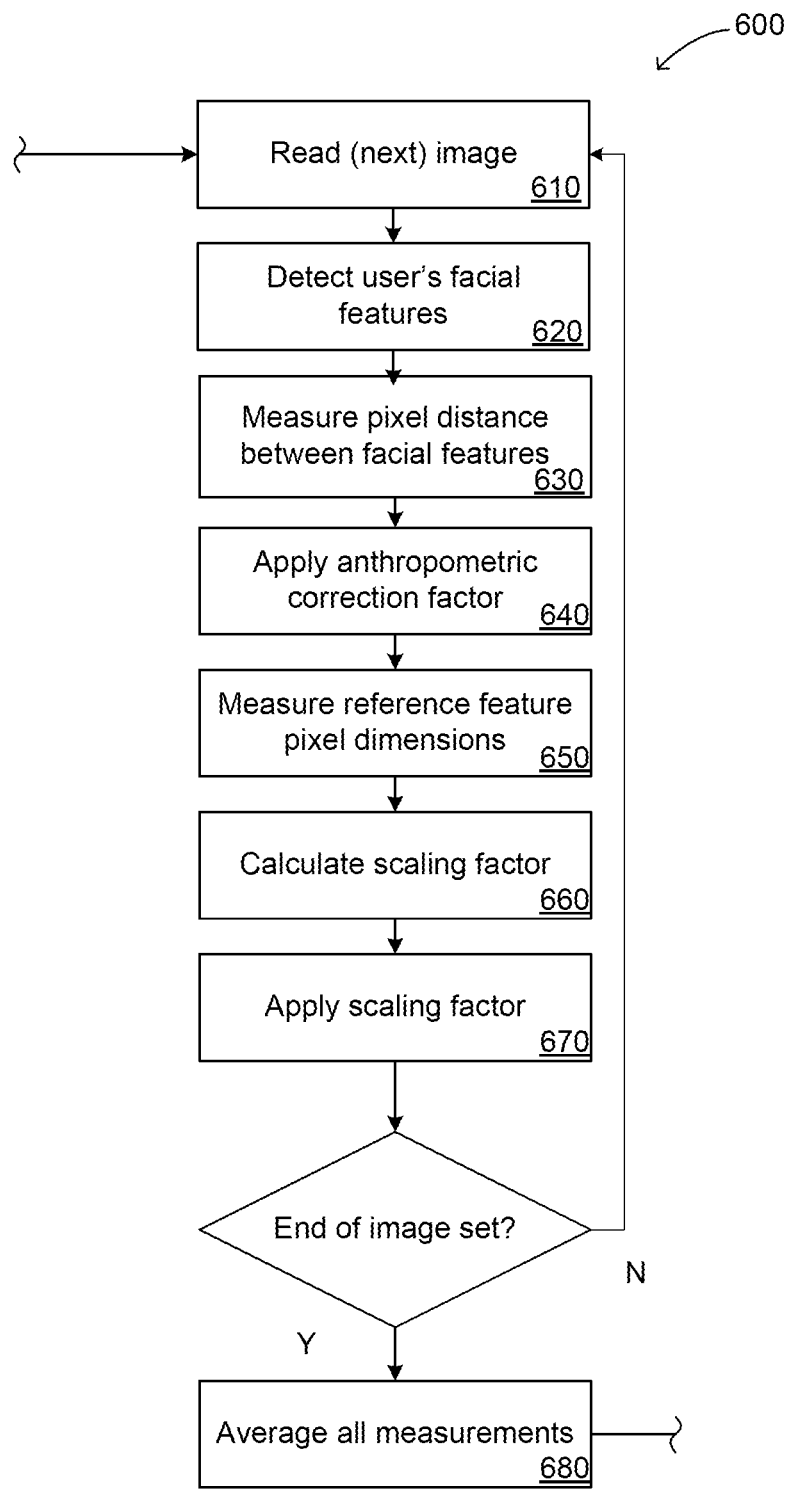
FIG. 6C is a flow diagram of a post-capture image processing phase method of some versions of the present technology.
Figure 6D:
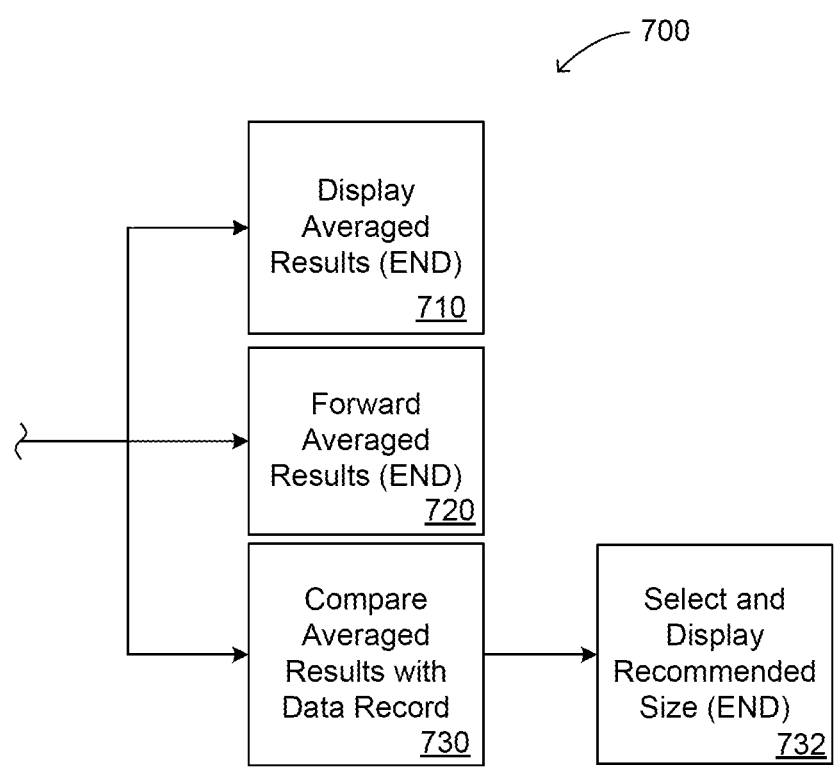
FIG. 6D is a flow diagram of a comparison and output phase method of some versions of an exemplary method embodiment of the present technology.

In the pre-capture phase, which is represented by the flow diagram of FIG. 6A, processor 310, among other things, assists the user in establishing the proper conditions for capturing one or more images for sizing processing. Some of these conditions include proper lighting and camera orientation and motion blur caused by an unsteady hand holding the computing device 230, for example.

In one version of the method, a user may conveniently download an application for performing the automatic measuring and sizing at computing device 230 from a server, such as a third party application-store server, onto their computing device 230. When downloaded, such application may be stored on the computing device's internal non-volatile memory, such as RAM or flash memory. Computing device 230 is preferably a mobile device, such as smartphone 234 or tablet 236. When the user launches the application, processor 310 may prompt the user via the computing device's display interface 320 to provide patient specific information, such as age, gender, weight, and height. However, processor 310 may prompt to the user to input this information at any time, such as after the user's facial features are measured. Processor 310 may also present a tutorial, which may be presented audibly and/or visually, as provided by the application to aid the user in understanding their role during the process. The prompts may also require information for patient interface type, e.g. nasal or full face, etc. and of the type of device for which the patient interface will be used. Also, in the pre-capture phase 400, the application may extrapolate the patient specific information based on information already gathered by the user, such as after receiving captured images of the user's face, and based on machine learning techniques or through artificial intelligence.

8.4.3.1.1 Sensor Activation 410

When the user is prepared to proceed, which may be indicated by a user input or response to a prompt via user control/input interface 331, processor 310 activates sensor 340 as instructed by the application's processor control instructions 352. Sensor 340 is preferably the mobile device's forward facing camera, which is located on the same side of the mobile device as display interface 320. The camera is generally configured to capture two-dimensional images. Mobile device cameras that capture two-dimensional images are ubiquitous. The present technology takes advantage of this ubiquity to avoid burdening the user with the need to obtain specialized equipment.

8.4.3.1.2 Display 420

Figure 7A:
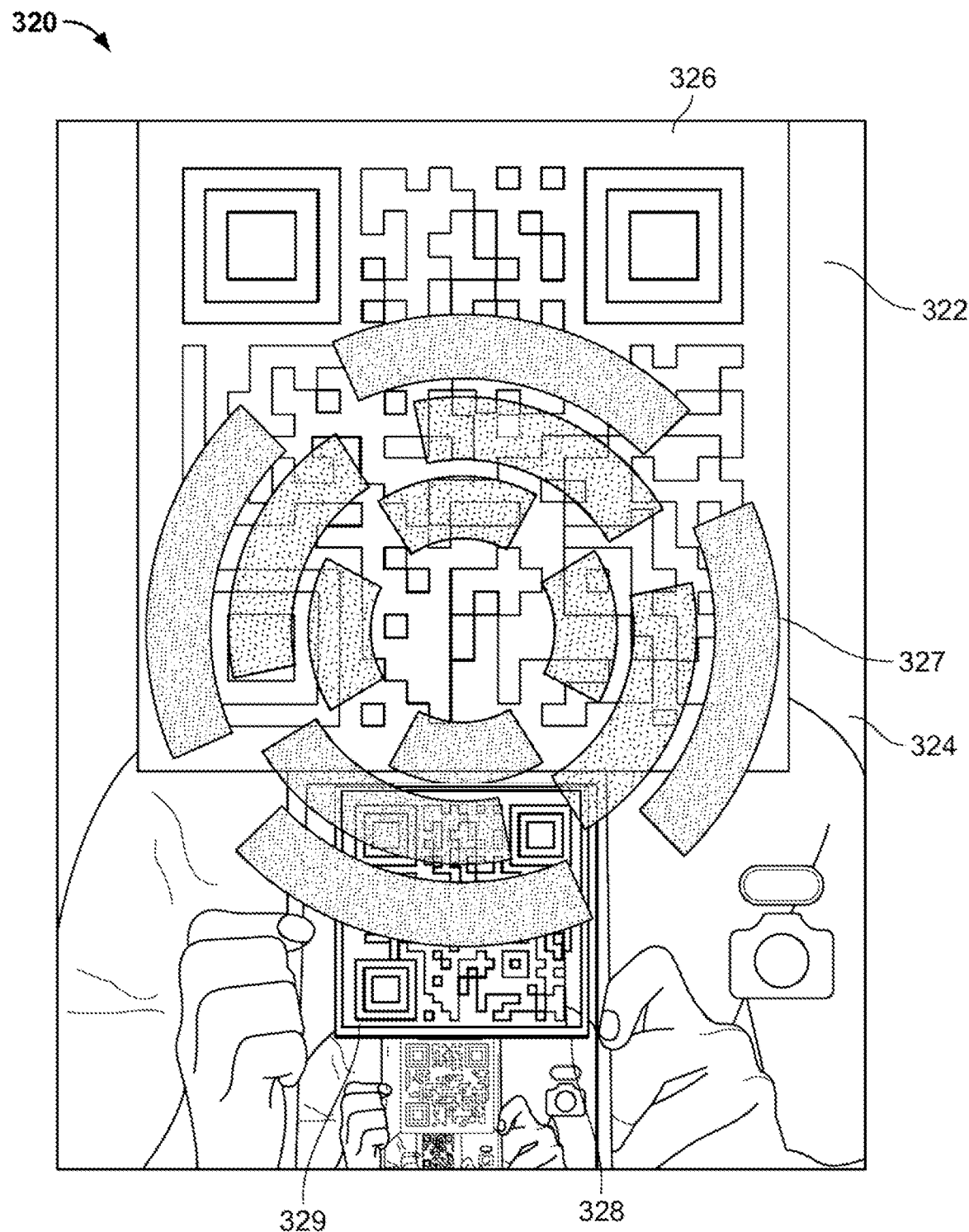
FIG. 7A shows an example display interface for some versions of the present technology.

Around the same time sensor/camera 340 is activated, processor 310, as instructed by the application, presents a capture display on the display interface 320. FIG. 7A depicts an example of a capture display 322 and of contents thereof, which may include a camera live action preview 324, a reference feature 326, a targeting box 328, and one or more status indicators 327 or any combination thereof. In this example, the reference feature 326 is displayed centred on the display interface and has a width corresponding to the width of the display interface 320. The vertical position of the reference feature 326 may be such that the top edge of reference feature 326 abuts the upper most edge of the display interface 320 or the bottom edge of reference feature 326 abuts the lower most edge of the display interface 320. A portion of the display interface 320 will display the camera live action preview 324, typically showing the user's facial features captured by sensor/camera 340 in real time if the user is in the correct position and orientation.

Live action preview 324 is a stream of images/content seen/detected by the camera/sensor 340 in, for example, real time. Thus, if the user directs the front facing camera 340 toward the user's facial features, the user's facial features may be presented on display interface 320. Similarly, if the user directs the front facing camera 340 toward a mirror 330, the reflection in the mirror 330, which would preferably include the display interface 320 and one or more of its contents including the reference feature 326, is displayed on the display interface 320 as part of live action preview 324. However, it should be understood that, while live action preview 324 can include the patient's facial features, it is not necessary to display such facial features on display interface 320, as is illustrated by FIG. 7A. Nevertheless, the sensor 340 does capture the facial features during this aspect of the process.

Reference feature 326 is a feature that is known to computing device 230 (predetermined) and provides a frame of reference to processor 310 that allows processor 310 to scale captured images. The reference feature may preferably be a feature other than a facial or anatomical feature of the user. Thus, during the image processing phase 600, it assists processor 310 in determining when certain alignment conditions are satisfied, such as during the pre-capture phase 400. As shown in FIG. 7A, reference feature 326 may be a quick response (QR) code or known exemplar or marker, which can provide processor 310 certain information, such as scaling information, orientation, and/or any other desired information which can optionally be determined from the structure of the QR code. The QR code may have a square or rectangular shape. When displayed on display interface 320, reference feature 326 has predetermined dimensions, such as in units of millimeters or centimeters, the values of which may be coded into the application and communicated to processor 310 at the appropriate time. The actual dimensions of reference feature 326 may vary between various computing devices. In some versions, the application may be configured to be a computing device model-specific in which the dimensions of reference feature 326, when displayed on the particular model, is already known. However, in other embodiments, the application may instruct processor 310 to obtain certain information from device 230, such as display size and/or zoom characteristics that allow the processor 310 to compute the real world/actual dimensions of reference feature 326 as displayed on display interface 320 via scaling. Regardless, the actual dimensions of reference feature 326 as displayed on the display interfaces 320 of such computing devices are generally known prior to post-capture image processing.

Along with reference feature 326, targeting box 328 may be displayed on display interface 320 and overlie live action preview 324. Targeting box 328 allows the user to align certain components within capture display 322 in targeting box 328, which is desired for successful image capture. In one example illustrated by FIG. 7A, the application may include a capture condition that reference feature 326 will be entirely within target box 328 prior to image capture. Alignment of reference feature 326 within targeting box 328 may improve detection during later processing and ensure good position and alignment of reference feature 326 within the captured image. Additionally, alignment within targeting box 328 may help to ensure display interface 320 alignment along a superior-inferior axis so as to avoid excessive radial inward or outward tilt and rotationally about the superior-inferior axis to maintain display interface 320 generally parallel with a mirror 330, for example.

The status indicator 327 provides information to the user regarding the status of the process. This helps ensure the user does not make major adjustments to the positioning of the sensor/camera prior to completion of image capture.

Thus, in the embodiment depicted in FIG. 7A, when the user holds display interface 320 parallel to the facial features to be measured and presents user display interface 320 to a mirror 330 or other reflective surface, reference feature 326 is prominently displayed and overlays the real-time images seen by camera/sensor 340 and as reflected by the mirror 330. This reference feature 326 may be fixed near the top of display interface 320. Reference feature 326 is prominently displayed in this manner at least partially so that sensor 340 can clearly see reference feature 326 so that processor 310 can easily identify feature 326. In addition, reference feature 326 may overlay the live view of the user's face, which helps avoid user confusion. A moveable reference feature image 329, which is a real-time live view reflection of reference feature 326, is positionable within the alignment box by movement of the display device having the image sensor. Ultimately, when movable reference feature image 329 is positioned within targeting box 328, alignment box and moveable reference feature image 329 will be positioned and aligned in an offset manner relative to reference feature 326 (e.g., directly below), which facilitates usability.

Other features or information can be displayed by processor 310 on display interface 320. For instance, the application may establish parameters that must be satisfied regarding lighting conditions. If lighting conditions are unsatisfactory, processor 310 may display a warning on the display interface or output an audible warning to the user and instruct the user on steps that can be taken that can help rectify the unsatisfactory lighting conditions.

Figure 7B:
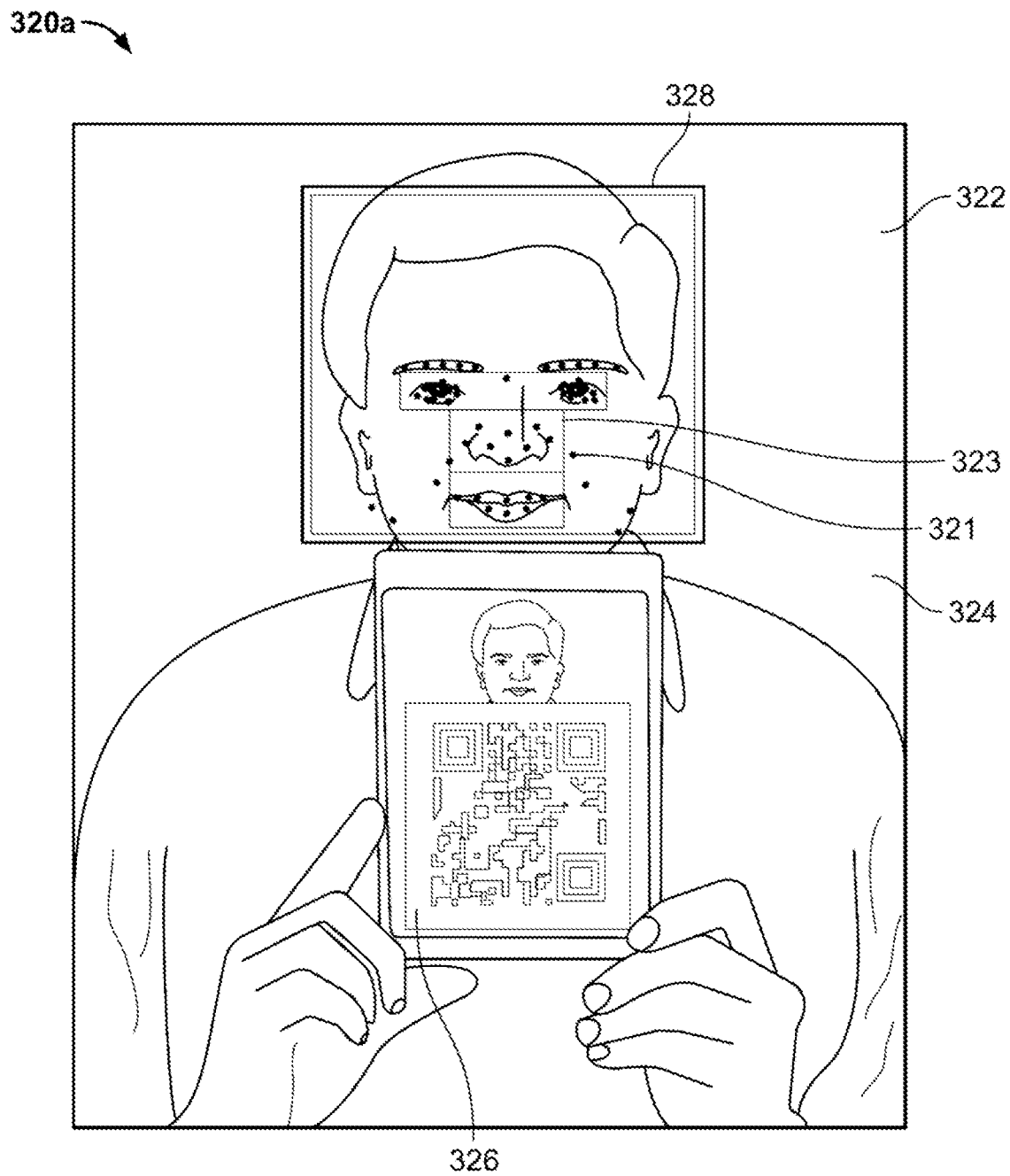
FIG. 7B shows another example display interface for some versions of the present technology.

FIG. 7B illustrates an alternative capture display embodiment 320a, which similarly includes a targeting box 328 and a reference feature 326. However, unlike FIG. 7A, live action preview 324 shows the user's face, which in this case is alternatively designated for placement within targeting box 328, rather than being designated to contain reference feature 326. Further, display 320a also includes detection points 321 and bounding boxes 323 generated by the processor 310. Processor 310, controlled by instructions from the application, may detect and identify certain facial features in live action preview 324. These may be displayed for the user using detection points 321 and bounding boxes 323. This may help the user know that certain conditions, such as lighting, are satisfactory for image capture as it indicates that processor 310 is identifying these facial features with detection points 321 and bounding them in bounding boxes 323.

8.4.3.1.3 Planar Alignment and Reflected Image 430

Figure 7C:
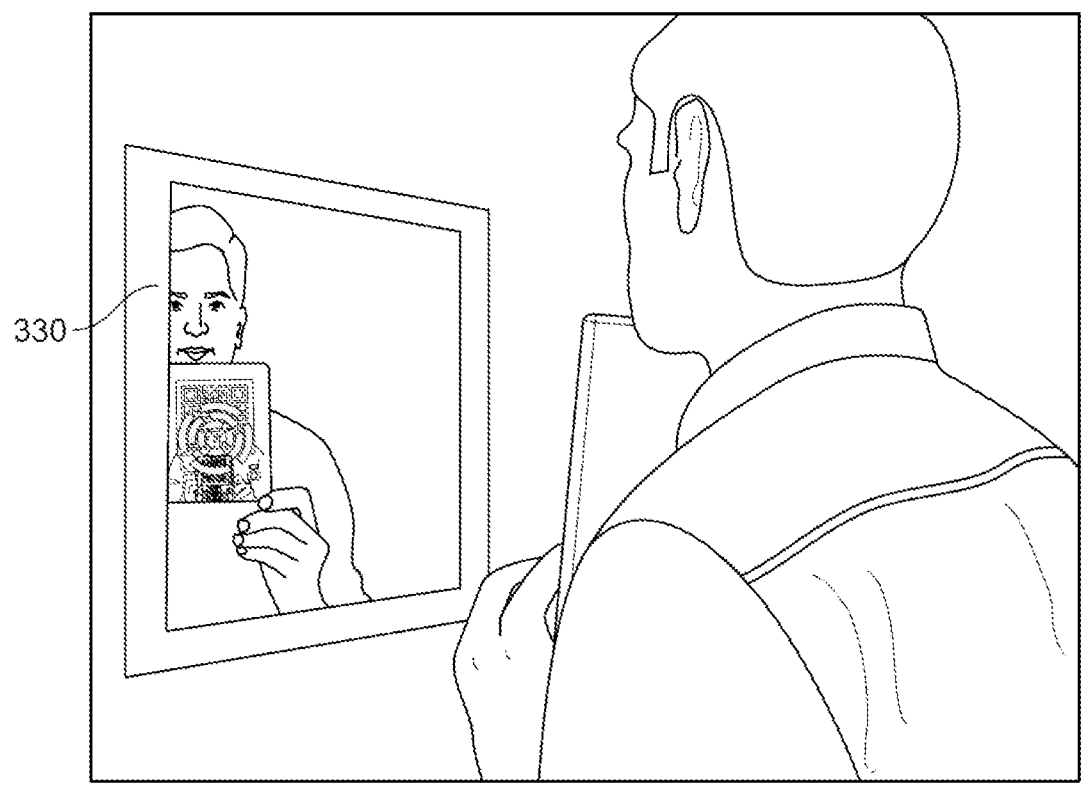
FIG. 7C illustrates a user employing a method of the present technology.

As depicted in FIG. 7C, the user may position themselves or their face and computing device 230 in front of a mirror 330 such that the user's facial features and display interface 320 are reflected back to sensor 340. The user may also be instructed by processor 310, via display interface 320, by audible instructions via a speaker of the computing device 230, or be instructed ahead of time by the tutorial, to position display interface 320 in a plane of the facial features to be measured. For example, the user may instructed to position display interface 320 such that it is facing anteriorly and placed under, against, or adjacent to the user's chin in a plane aligned with certain facial features to be measured. For example, display interface 320 may be placed in planar alignment with the sellion and supremention. As the images ultimately captured are two-dimensional, planar alignment 430 helps ensure that the scale of reference feature 326 is equally applicable to the facial feature measurements. In this regard, the distance between the mirror 330 and both of the user's facial features and the display will be approximately the same.

8.4.3.1.4 Detecting Reference Feature 440

When the user is positioned in front of a mirror 330 and display interface 320, which includes reference feature 326, is roughly placed in planar alignment with the facial features to be measured, processor 310 checks for certain conditions to help ensure sufficient alignment. One exemplary condition that may be established by the application, as previously mentioned, is that the entirety of reference feature 326 must be detected within targeting box 328 in order to proceed. If processor 310 detects that reference feature 326 is not entirely positioned within targeting box 328, processor may 310 prohibit or delay image capture. The user may then move their face along with display interface 320 to maintain planarity until reference feature 326, as displayed in the live action preview, is located within targeting box 328. This helps optimized alignment of the facial features and display interface 320 with respect to mirror 330 for image capture.

8.4.3.1.5 Reading IMU & Tilt Alignment 450

When processor 310 detects the entirety of reference feature 326 within targeting box 328, processor 310 may read the computing device's IMU 342 for detection of device tilt angle, provided that computing device 230 includes an IMU 342. The IMU 342 may include an accelerometer or gyroscope, for example. Thus the processor 310 may evaluate device tilt such as by comparison against one or more thresholds to ensure it is in a suitable range. For example, if it is determined that computing device 230, and consequently display interface 320 and user's facial features, is tilted in any direction within about +/−5 degrees, the process may proceed to the capture phase 500. In other embodiments, the tilt angle for continuing may be within about +/−10 degrees, +/−7 degrees, +/−3 degrees, or +/−1 degree. If excessive tilt is detected a warning message may be displayed or sounded to correct the undesired tilt. This is particularly useful for assisting the user to help prohibit or reduce excessive tilt, particularly in the anterior-posterior direction, which if not corrected, could pose as a source of measuring error as the captive reference image will not have a proper aspect ratio.

8.4.3.2 Capture Phase 500

8.4.3.2.1 Capture Initiation 510

When alignment has been determined by processor 310 as controlled by the application, processor 310 proceeds into the capture phase 500. This phase 500 preferably occurs automatically once the alignment parameters and any other conditions precedent are satisfied. However, in some embodiments, the user may initiate the capture in response to a prompt to do so.

8.4.3.2.2 Capture "n" Images 520

When image capture is initiated, the processor 310 via sensor 340 captures a number n of images, which is preferably more than one image. For example, the processor 310 via sensor 340 may capture about 5 to 20 images, 10 to 20 images, or 10 to 15 images, etc. The quantity of images captured may be time-based. In other words, the number of images that are captured may be based on the number of images of a predetermined resolution that can be captured by sensor 340 during a predetermined time interval. For example, if the number of images sensor 340 can capture at the predetermined resolution in 1 second is 40 images and the predetermined time interval for capture is 1 second, sensor 340 will capture 40 images for processing with processor 310. The quantity of images may be user-defined, determined by server 210 based on artificial intelligence or machine learning of environmental conditions detected, or based on an intended accuracy target. For example, if high accuracy is required then more captured images may be required. Although, it is preferable to capture multiple images for processing, one image is contemplated and may be successful for use in obtaining accurate measurements. However, more than one image allows average measurements to be obtained. This may reduce error/inconsistencies and increase accuracy. The images may be placed by processor 310 in stored data 354 of memory/data storage 350 for post-capture processing.

8.4.3.3 Post-Capture Image Processing Phase 600

Once the images are captured, the images are processed by processor 310 to detect or identify facial features/landmarks and measure distances therebetween. The resultant measurements may be used to recommend an appropriate patient interface size. This processing may alternatively be performed by server 210 receiving the transmitted captured images and/or on the user's computing device (e.g., smart phone). Processing may also be undertaken by a combination of the processor 310 and server 210. In one example, the recommended patient interface size may be predominantly based on the user's nose width. In other examples, the recommended patient interface size may be based on the user's mouth and/or nose dimensions.

8.4.3.3.1 Read Images and Detect Facial Features 610 & 620

Processor 310, as controlled by the application, retrieves one or more captured images from stored data 354. The image is then extracted by processor 310 to identify each pixel comprising the two-dimensional captured image. Processor 310 then detects certain pre-designated facial features within the pixel formation. Detection may be performed by processor 310 using edge detection, such as Canny, Prewitt, Sobel, or Robert's edge detection, for example. These edge detection techniques/algorithms help identify the location of certain facial features within the pixel formation, which correspond to the patient's actual facial features as presented for image capture. For example, the edge detection techniques can first identify the user's face within the image and also identify pixel locations within the image corresponding to specific facial features, such as each eye and borders thereof, the mouth and corners thereof, left and right alares, sellion, supramenton, glabella and left and right nasolabial sulci, etc. Processor 310 may then mark, tag or store the particular pixel location(s) of each of these facial features. Alternatively, or if such detection by processor 310/server 210 is unsuccessful, the pre-designated facial features may be manually detected and marked, tagged or stored by a human operator with viewing access to the captured images through a user interface of the processor 310/server 210.

8.4.3.3.2 Measure Distance Between Facial Features 630

Once the pixel coordinates for these facial features are identified, the application controls processor 310 to measure the pixel distance between certain of the identified features. For example, the distance may generally be determined by the number of pixels for each feature and may include scaling. For example, measurements between the left and right alares may be taken to determine pixel width of the nose and/or between the sellion and supramenton to determine the pixel height of the user's face. Other examples include pixel distance between each eye, between mouth corners, and between left and right nasolabial sulci to obtain additional measurement data of particular structures like the mouth. Further distances between facial features can be measured.

8.4.3.3.3 Apply Anthropometric Correction Factor 640

Once the pixel measurements of the pre-designated facial features are obtained, an anthropometric correction factor(s) may be applied to the measurements. It should be understood that this correction factor can be applied before or after applying a scaling factor, as described below. The anthropometric correction factor can correct for errors that may occur in the automated process, which may be observed to occur consistently from patient to patient. In other words, without the correction factor, the automated process, alone, may result in consistent results from patient to patient, but results that may lead to a certain amount of mis-sized patient interfaces. The correction factor, which may be empirically extracted from population testing, shifts the results closer to a true measurement helping to reduce or eliminate mis-sizing. This correction factor can be refined or improved in accuracy over time as measurement and sizing data for each patient is communicated from respective computing devices to server 210 where such data may be further processed to improve the correction factor. The anthropometric correction factor may also vary between the forms of patient interfaces. For instance, the correction factor for a particular patient seeking an FFM may be different from the correction factor when seeking a nasal mask. Such a correction factor may be derived from tracking of mask purchases, such as by monitoring mask returns and determining the size difference between a replacement mask and the returned mask.

8.4.3.3.4 Measure Reference Feature 650

In order to apply the facial feature measurements to patient interface sizing, whether corrected or uncorrected by the anthropometric correction factor, the measurements may be scaled from pixel units to other values that accurately reflect the distances between the patient's facial features as presented for image capture. The reference feature may be used to obtain a scaling value or values. Thus, processor 310 similarly determines the reference feature's dimensions, which can include pixel width and/or pixel height (x and y) measurements (e.g., pixel counts) of the entire reference feature. More detailed measurements of the pixel dimensions of the many squares/dots that comprise a QR code reference feature 326, and/or pixel area occupied by the reference feature and its constituent parts may also be determined. Thus, each square or dot of the QR code reference feature 326 may be measured in pixel units to determine a scaling factor based on the pixel measurement of each dot and then averaged among all the squares or dots that are measured, which can increase accuracy of the scaling factor as compared to a single measurement of the full size of the QR code reference feature 326. However, it should be understood that whatever measurements are taken of the reference feature, the measurements may be utilized to scale a pixel measurement of the reference feature to a corresponding known dimension of the reference feature.

8.4.3.3.5 Calculate Scaling Factor 660

Once the measurements of the reference feature are taken by processor 310, the scaling factor is calculated by processor 310 as controlled by the application. The pixel measurements of reference feature are related to the known corresponding dimensions of the reference feature, e.g. the reference feature 326 as displayed by display interface 320 for image capture, to obtain a conversion or scaling factor. Such a scaling factor may be in the form of length/pixel or area/pixel^2. In other words, the known dimension(s) may be divided by the corresponding pixel measurement(s) (e.g., count(s)).

8.4.3.3.6 Apply Scaling Factor 670

Processor 310 then applies the scaling factor to the facial feature measurements (pixel counts) to convert the measurements from pixel units to other units to reflect distances between the patient's actual facial features suitable for mask sizing. This may typically involve multiplying the scaling factor by the pixel counts of the distance(s) for facial features pertinent for mask sizing.

These measurement steps and calculation steps for both the facial features and reference feature are repeated for each captured image until each image in the set has facial feature measurements that are scaled and/or corrected.

8.4.3.3.7 Average Facial Feature Measurements 680

The corrected and scaled measurements for the set of images may then optionally be averaged by processor 310 to obtain final measurements of the patient's facial anatomy. Such measurements may reflect distances between the patient's facial features.

8.4.3.4 Comparison and Output Phase 700

In the comparison and output phase 700, results from the post-capture image processing phase 600 may be directly output (displayed) to a person of interest or compared to data record(s) to obtain an automatic recommendation for a patient interface size.

8.4.3.4.1 Display Averaged Results 710

Once all of the measurements are determined, the results (e.g., averages) may be displayed by processor 310 to the user via display interface 320. In one embodiment, this may end the automated process. The user/patient can record the measurements for further use by the user.

8.4.3.4.2 Forward Averaged Results 720

Alternatively, the final measurements may be forwarded either automatically or at the command of the user to server 210 from computing device 230 via communication network 220. Server 210 or individuals on the server-side may conduct further processing and analysis to determine a suitable patient interface and patient interface size.

8.4.3.4.3 Compare Results, Select and Display Recommended Size 730 & 732

In a further embodiment, the final facial feature measurements that reflect the distances between the patient's actual facial features are compared by processor 310 to patient interface size data such as in a data record. The data record may be part of the application for automatic facial feature measurements and patient interface sizing. This data record can include, for example, a lookup table accessible by processor 310, which may include patient interface sizes corresponding to a range of facial feature distances/values. Multiple tables may be included in the data record, many of which may correspond to a particular form of patient interface and/or a particular model of patient interface offered by the manufacturer.

Processor 310 compares the user's measurements to determine an appropriate size or "best fit," such as by identifying one or more ranges within which the measurements fall and then selecting the interface size, such as from a group of standard sizes (e.g., small, medium, or large, etc.), associated with that identified range(s). Processor 310 may then recommend the identified patient interface size in the form of a display presented on display interface 320. Processor 310 may even automatically forward the recommendation via email, text message or instant messenger for the user's records. The user may further have the option provided to it via processor 310 to order a patient interface with the recommended size. The order may be communicated to server 210 where further steps for order fulfilment may take place.

8.4.4 Alternatives and Additional Application Features

The following describes additional and/or alternative features that may be implemented with the above described example methods, systems and devices. The below are not intended to be exhaustive, but are merely examples of the many variations that can be achieved while conforming to the present technology.

8.4.4.1 Alternative Computing Devices

In the above examples, the method is at least in part performed by a mobile device as computing device 230. However, the facial feature measuring and/or interface sizing can be performed, at least in part, with desktop or laptop 232, for example. In such example, the image capture and post-image processing phases 500, 600 would be similar to that described above. However, the method may differ in the pre-capture phase 400. In this phase, rather than displaying reference feature 326 on display interface 320 and positioning display interface 320 and user's facial features in front of mirror 330 so that reference feature 326 is captured in the image, the reference feature can be printed onto a sheet of paper at a known scale and held by the user. As such, webcam 233 could display, via processor 310, a live action preview of the user and the reference feature on the display interface, which may be a monitor. A targeting box, similar to that described above, would also be displayed, in which case the user may reposition themselves and the reference feature so that the reference feature or user's face is positioned within the targeting box.

8.4.4.2 Alternative Reference Features

While example reference feature 326 displayed by display interface 320 described above may include a QR code or other processor detectable reference feature, other reference features of known dimensions, either displayed by display interface 320 or positioned in close proximity to the user, may be utilized. When the reference feature is not a displayed feature captured through a mirror 330, the reference feature may be a known physical feature, suggested by the application, and positioned near the user. For example, a sheet of paper, coin, credit card or cardboard cut-out with a QR code superimposed thereon may be used as a reference feature. While such close-positioned reference features could be used in the method implementing a mirror 330, such reference features could be particularly useful in a desktop computing device method described directly above. In one example a user may hold up a credit card of known size (standard) such that the processor may detect the card as the reference feature for purposes of determining a scaling factor. In another embodiment, a sheet of paper of known size, such as size A4 paper, can be held in either landscape or portrait orientation. Processor, via sensor 233 may detect corners and/or aspect ratio of the paper to determine when it is aligned with an alignment box as a precondition to image capture and/or to determine a scaling factor from one or more images including the paper reference feature, which is of known size. A further implementation in which a coin is used as the reference feature is described in more detail below.

8.4.4.2.1 Coin

Figure 8:
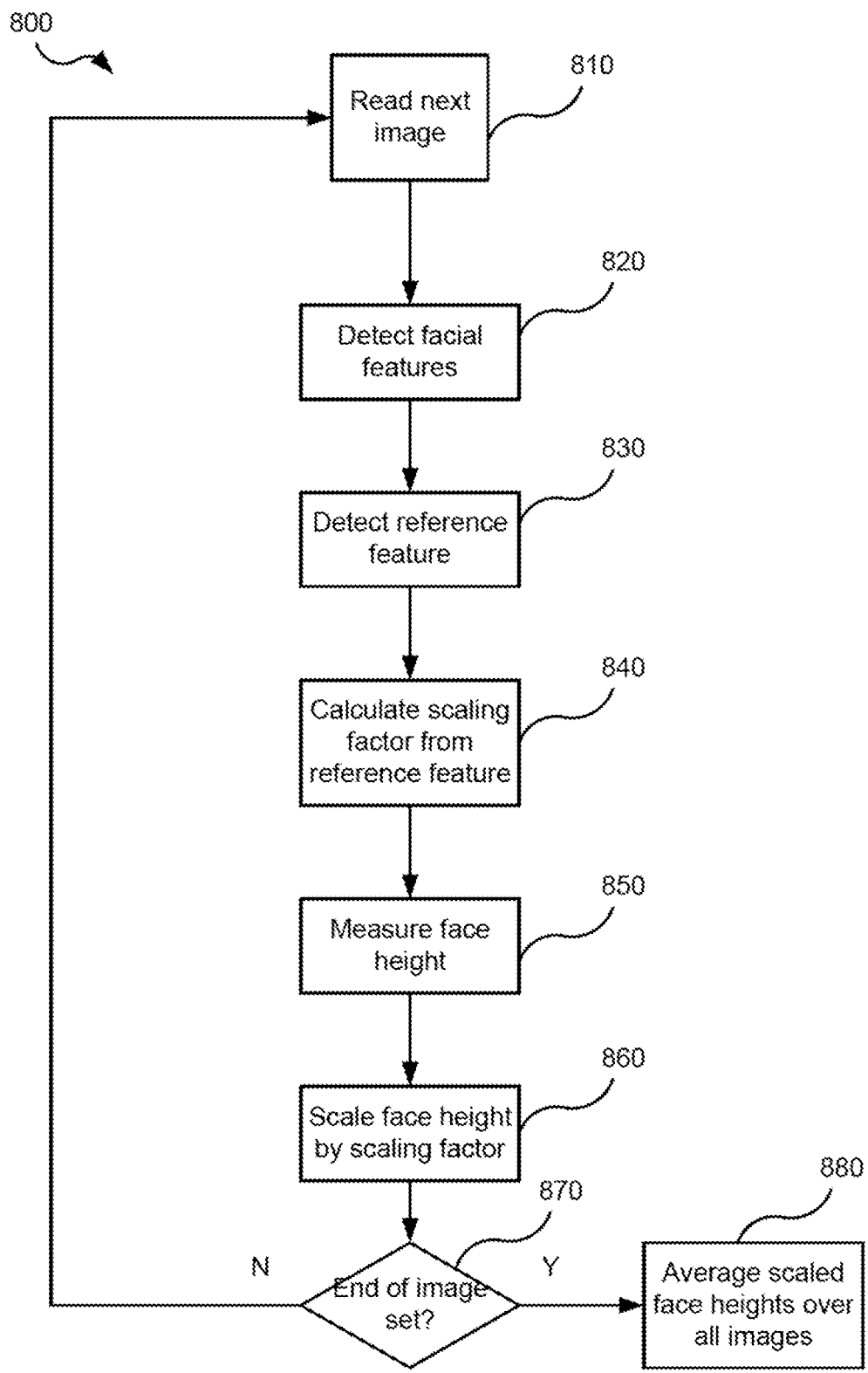
FIG. 8 is a flow diagram of a method of implementing the post-capture image processing phase according to a further implementation of the present technology.
Figure 13A:
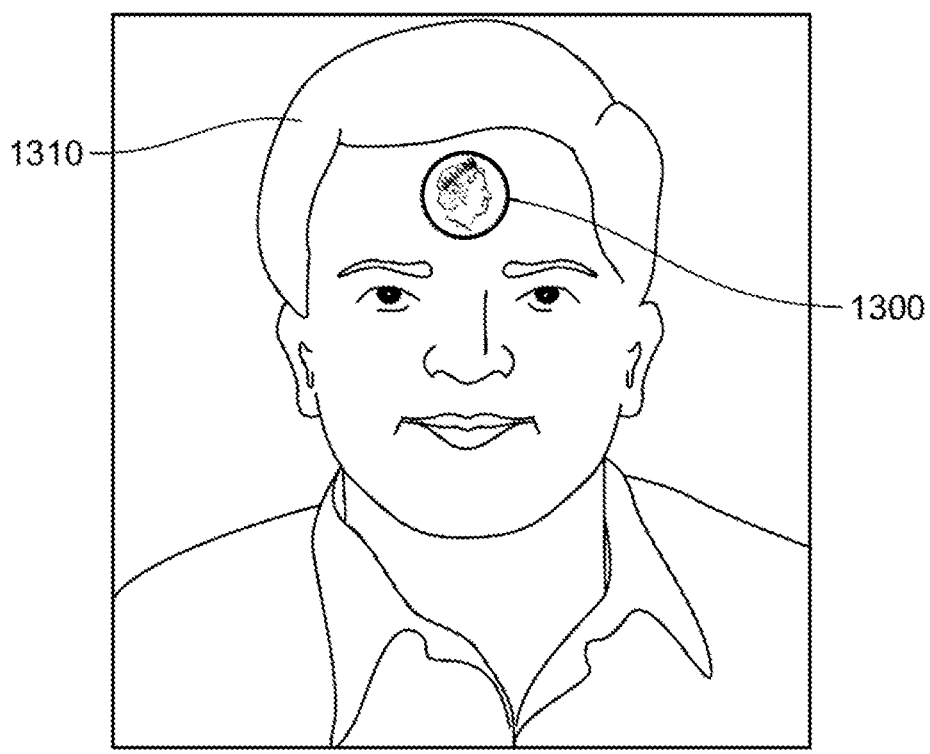
FIG. 13A is an illustration of the positioning of a coin on the user's forehead according to the further implementation of the present technology.

FIG. 8 contains a flow chart illustrating a method 800 that may be used in place of the process 600 to implement the post-capture image processing phase in an implementation in which a coin is used as the reference feature. In such an implementation, there is no need for the pre-capture phase 400. The coin 1300 is placed on the user's forehead 1310 approximately above the nose, as illustrated in FIG. 13A, prior to the image capture phase 500 described above. Under normal skin conditions the coin will adhere to the user's forehead 1310 for sufficient time to complete the image capture phase 500. The method 800 is then carried out to implement the post-capture image processing phase, and finally the comparison and output phase 700 is carried out as described above.

The method 800 starts at step 810, which is the first step of a loop over all images captured during the image capture phase. Step 810 reads the next captured image. Step 820 detects facial features (eyes and mouth) in the captured image. Step 820 will be described in more detail below with reference to FIG. 9. Step 830 detects the reference feature (the coin) in the captured image. Step 830 will be described in more detail below with reference to FIG. 10. Step 840 uses the reference feature to calculate a scaling factor. Step 840 will be described in more detail below with reference to FIG. 11. The next step 850 makes a measurement of the facial features detected in the captured image at step 820. Step 850 may alternatively be performed before steps 830 and 840. Step 850 will be described in more detail below with reference to FIG. 12. Step 860 then multiplies the facial feature measurement made at step 850 by the scaling factor calculated at step 840. Step 870 checks whether the end of the captured image set has been reached. If not ("N"), the method 800 returns to step 810 to read the next captured image. Otherwise ("Y"), the final step 880 averages the scaled facial feature measurements for all captured images to produce a final scaled facial feature measurement ready for the comparison and output phase 700 described above.

Figure 9:
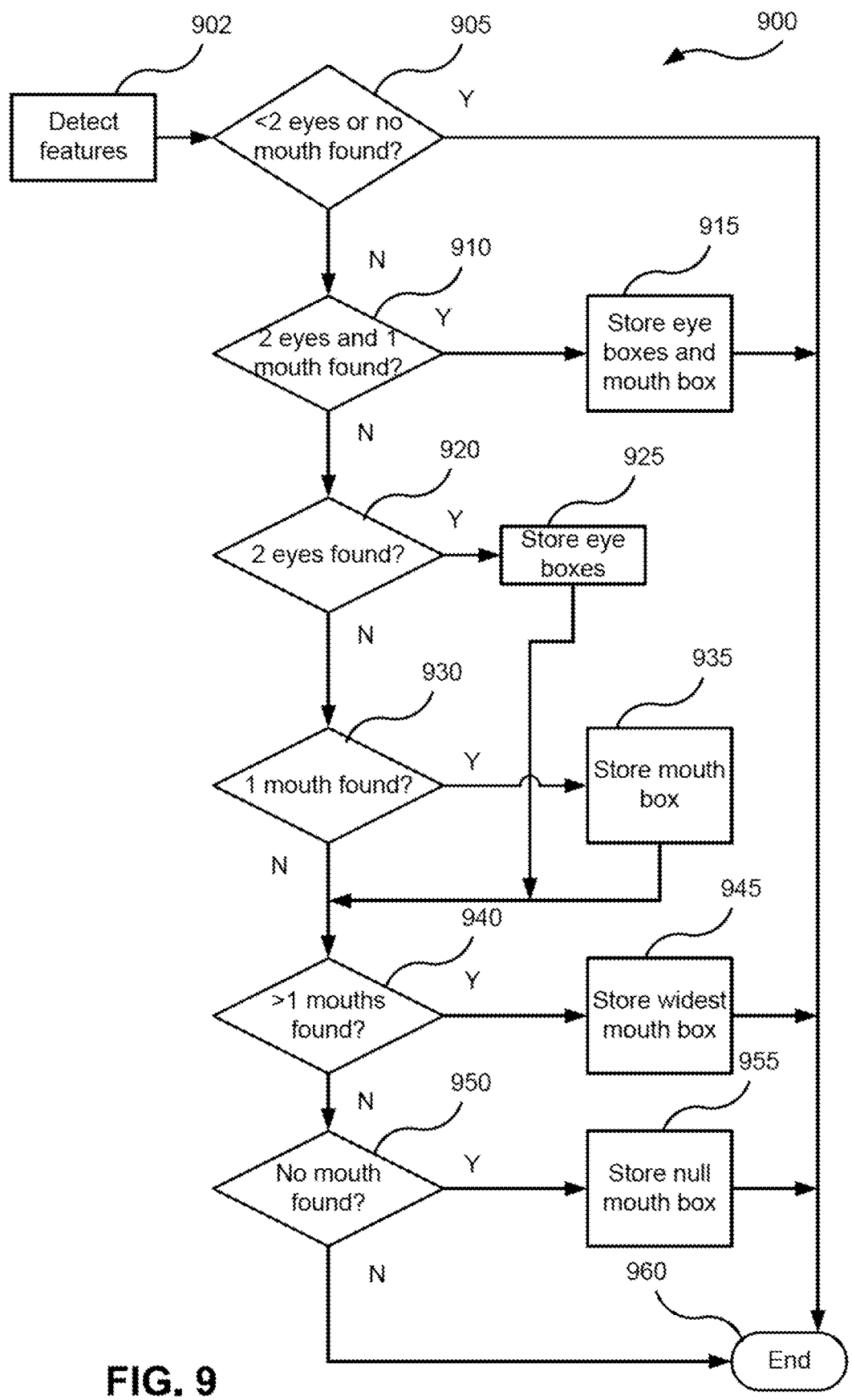
FIG. 9 is a flow chart illustrating a method of implementing the facial feature detection step of the method of FIG. 8.

FIG. 9 contains a flow chart illustrating a method 900 that may be used to implement the facial feature detection step 820 of the method 800 according to one implementation. The method 900 starts at step 902, which detects the faces in the image. The faces within the image may be found, for example, using an OpenCV cascade classifier with thresholds on object size. Each pair of eyes and mouth within each detected face is found using corresponding cascade classifiers. This result of step 902 is a list of rectangles or "boxes" defining the boundary of each detected face within the image. For each detected face, a list of boxes defining the position and extent of the eye(s) and mouth(s) found within the face are returned by step 902. Step 902 also returns, for each detected face, a box for each coin found within the face. These boxes may be used by step 830 to detect the correct reference feature within the detected face.

The following steps 905 to 960 are carried out for the largest face box detected at step 902. Steps 905 to 960 filter the features detected within the face to choose only the "best" matches and remove any duplicates/incorrect matches.

Step 905 checks whether fewer than two eyes or no mouth was found by the face detection step 902. If so ("Y"), the method 900 ends at step 960. If not ("N"), step 910 checks whether exactly two eyes and one mouth were found at step 902. If so ("Y"), step 915 stores the two eye boxes and the mouth box, and the method 900 then ends at step 960. If not ("N"), step 920 checks whether two eyes were found at step 902. If so ("Y"), step 925 stores the two eye boxes, and the method 900 proceeds to step 940 described below. If not ("N"), step 930 checks whether one mouth was found at step 902. If so, step 935 stores the mouth box, and the method 900 proceeds to step 940. If not ("N"), step 940 checks whether more than one mouth was found at step 902. If so ("Y"), step 945 stores the widest mouth box of the multiple mouth boxes, and the method 900 then ends at step 960. Otherwise ("N"), step 950 checks whether no mouth was found at step 902. If so ("Y"), step 955 stores a null mouth box (with corners (0,0) and (0,0)), and the method 900 then ends at step 960. Otherwise ("N"), the method 900 ends at step 960.

In other cascade-classifier implementations of step 820, other criteria may be used to filter the boxes found within the largest face box at step 902 to return the most probable eye and mouth boxes.

Figure 10:
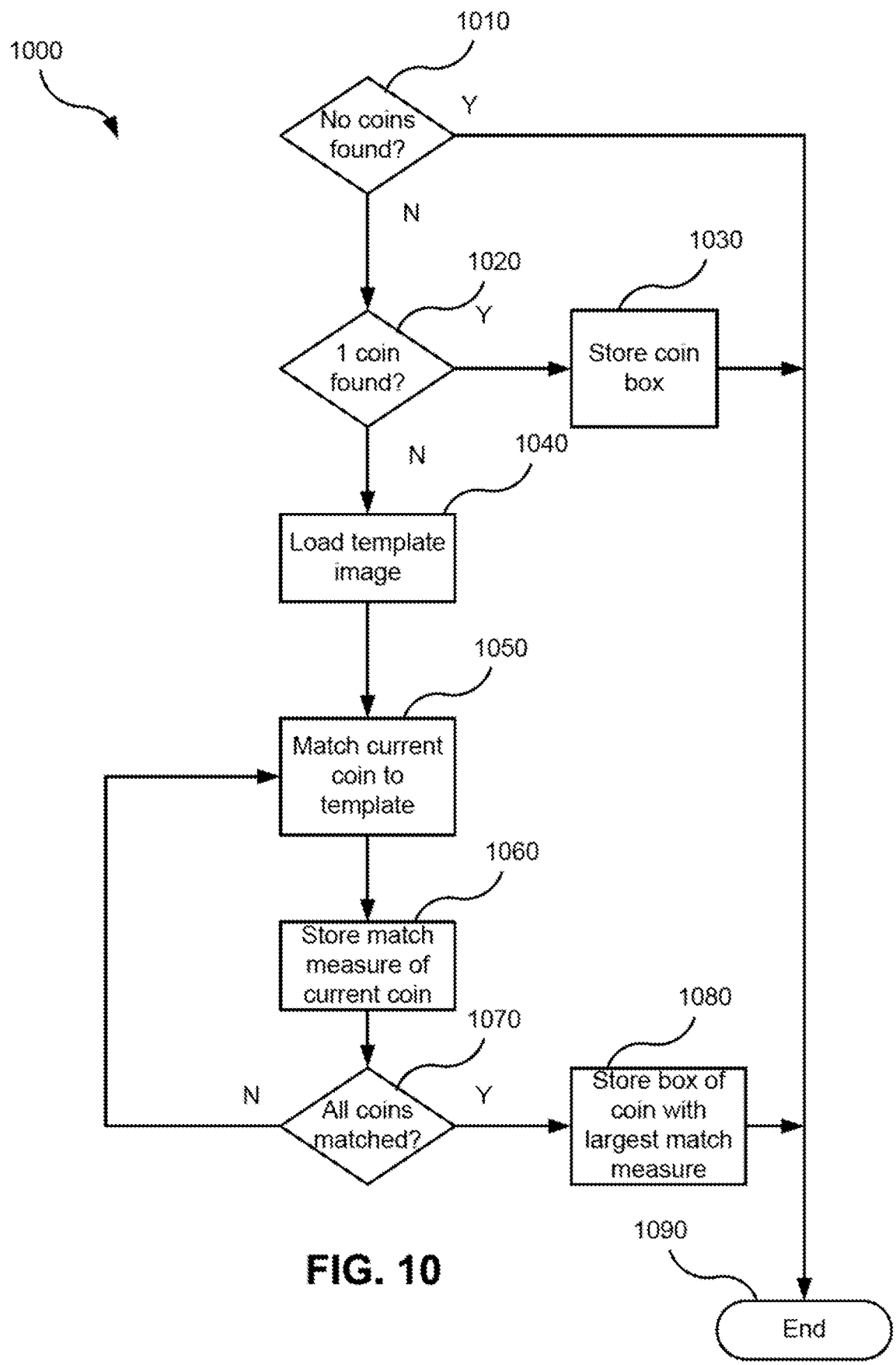
FIG. 10 is a flow chart illustrating a method of implementing the reference feature detection step of the method of FIG. 8.

FIG. 10 contains a flow chart illustrating a method 1000 that may be used to implement the reference feature detection step 830 of the method 800 according to the implementation of the method 800 in which the method 900 is used to implement the step 820. Steps 1010 to 1090 are carried out on the largest face box detected at step 902 of the method 900 to identify the "best" detected coin within the face. Step 1010 checks whether no coin was detected within the face at step 902. If so ("Y"), the method 1000 ends at step 1090. Otherwise ("N"), step 1020 checks whether exactly one coin was detected at step 902. If so ("Y"), step 1030 stores the coin box, and the method 1000 ends at step 1090. Otherwise ("N"), step 1040 loads a "template image", i.e. a reference image of the reference feature. Steps 1050 to 1070 are then carried out for each of the multiple coins detected in the face at step 902. Step 1050 computes a measure of match between the current coin and the reference image. In one implementation, step 1050 counts the number of matching points between the current coin and the reference image. Step 1060 then stores the measure of match found at step 1050. Step 1070 checks whether all the coins have been matched. If not ("N"), the method 1000 returns to step 1050. If so ("Y"), step 1080 finds the largest measure of match stored at step 1060, and stores the box of the coin with the largest match measure. The method 1000 then ends at step 1090.

Figure 11:
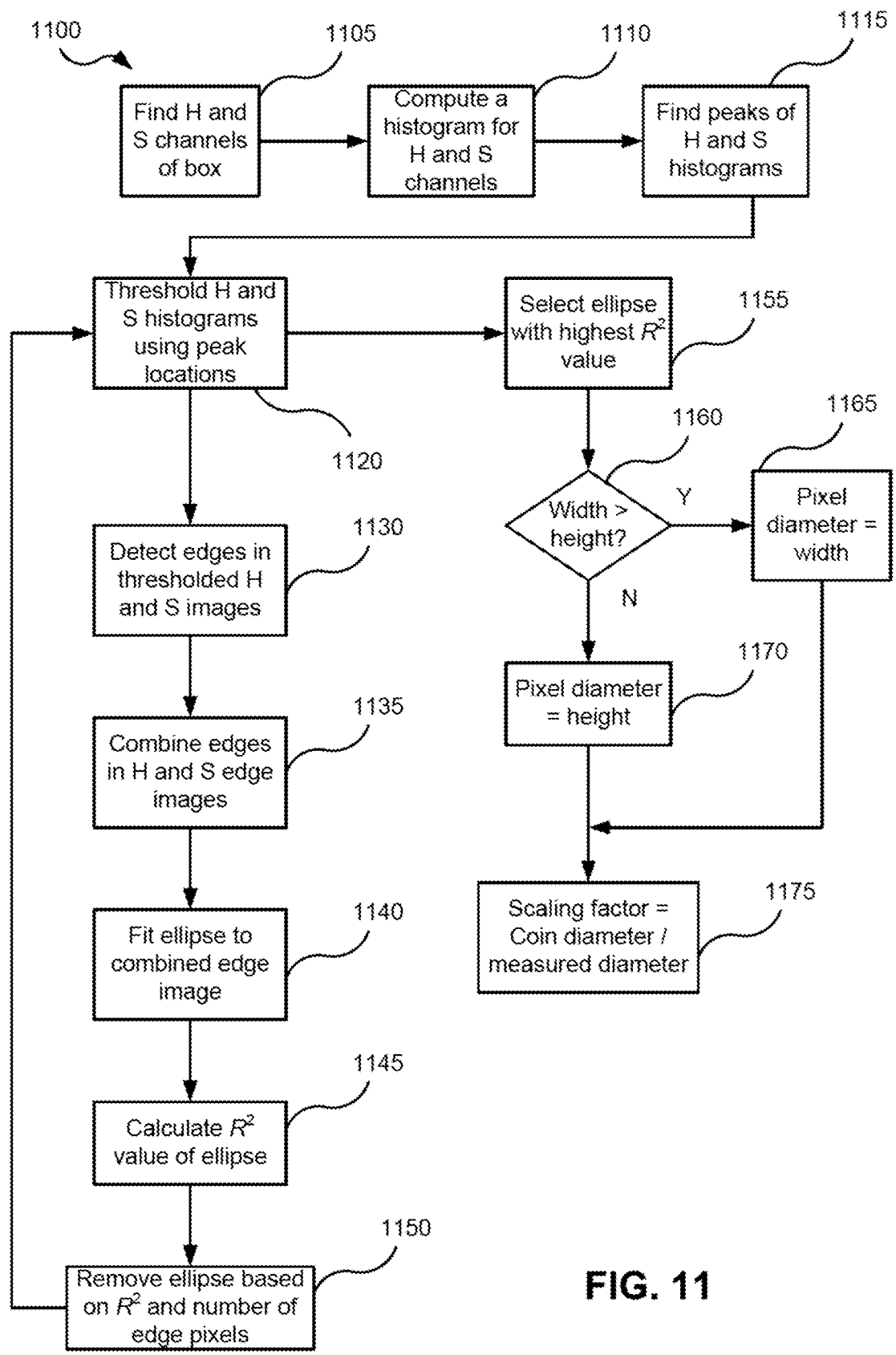
FIG. 11 is a flow chart illustrating a method of implementing the scaling factor calculation step of the method of FIG. 8.

FIG. 11 contains a flow chart illustrating a method 1100 that may be used to implement the calculating of a scaling factor step 840 of the method 800 according to one implementation. Steps 1105 to 1175 are carried out for the "best" coin detected at step 830. The first step 1105 converts the image contained within the coin box to separate hue (H) and saturation (S) channels. Step 1110 then computes a histogram for each of the H and S channels of the box. Then, step 1115 finds the peaks of the H and S channel histograms. Steps 1120 to 1150 are then carried out for each pair of peaks in the H and S channel histograms. Step 1120 thresholds the H and S channel images using thresholds equal to the current respective peak locations. Step 1130 then detects images in the thresholded (binary) H and S images. In one implementation, step 1130 uses a Canny edge detection filter on the binary images. Step 1135 then combines the two edge images using a binary "AND" operation, such that the only surviving edge pixels are those that were detected in both H and S binary images. The next step 1140 fits an ellipse to the combined edge image. Step 1140 may use any convenient method, e.g. linear regression, to fit an ellipse to the combined edge image. An ellipse is fit to the combined edge image at step 1140 because a circle rotated three-dimensionally through any angle appears as an ellipse. Step 1145 calculates the coefficient of determination (written as $R^2$) of the ellipse fitted at step 1140. Step 1150 then removes the ellipse if the coefficient of determination is too low or the number of edge pixels in the combined edge image is too low.

After the final pair of H, S histogram peaks has been processed, step 1155 selects the ellipse with the highest coefficient of determination. Step 1160 then compares the width (horizontal diameter) and height (vertical diameter) of the selected ellipse. If the width is greater than the height ("Y"), step 1165 sets the measured diameter of the coin to the width of the ellipse (as a pixel count). Otherwise ("N"), step 1170 sets the measured diameter of the coin to the height of the ellipse (as a pixel count). Finally, step 1175 calculates the scaling factor as the true diameter of the coin (a known quantity, e.g. in millimetres) divided by the measured diameter of the coin from step 1170 or step 1165.

This calculation is based on the fact that when a circular disc is rotated through any angle its projected outline appears as an ellipse, and the length of the major axis of the ellipse is the diameter of the disc regardless of the amount or direction of rotation. This fact underpins the suitability of circular reference features such as coins for calculating scaling factors for image measurements.

Figure 12:
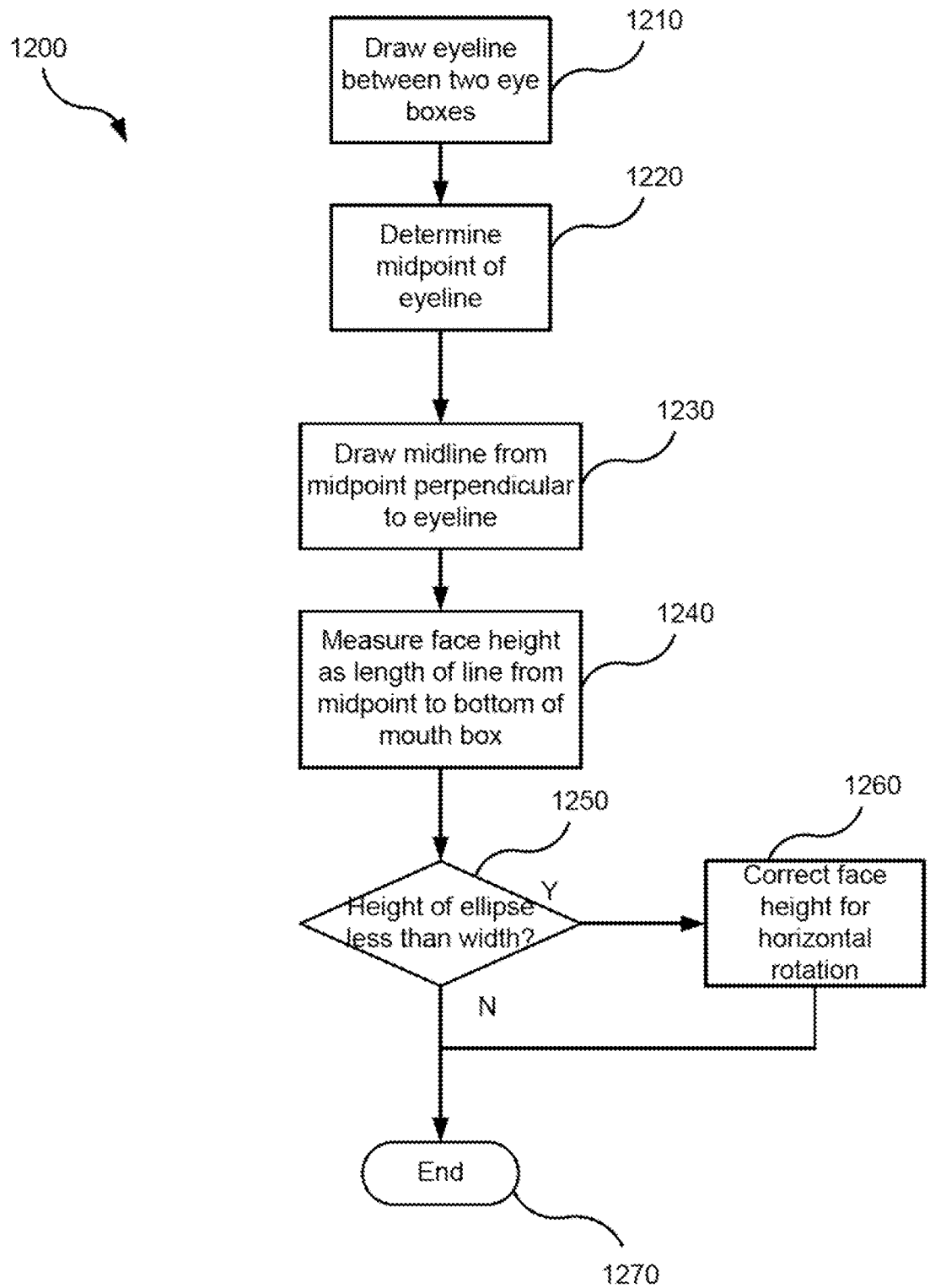
FIG. 12 is a flow chart illustrating a method of implementing the facial feature measurement step of the method of FIG. 8.
Figure 13B:
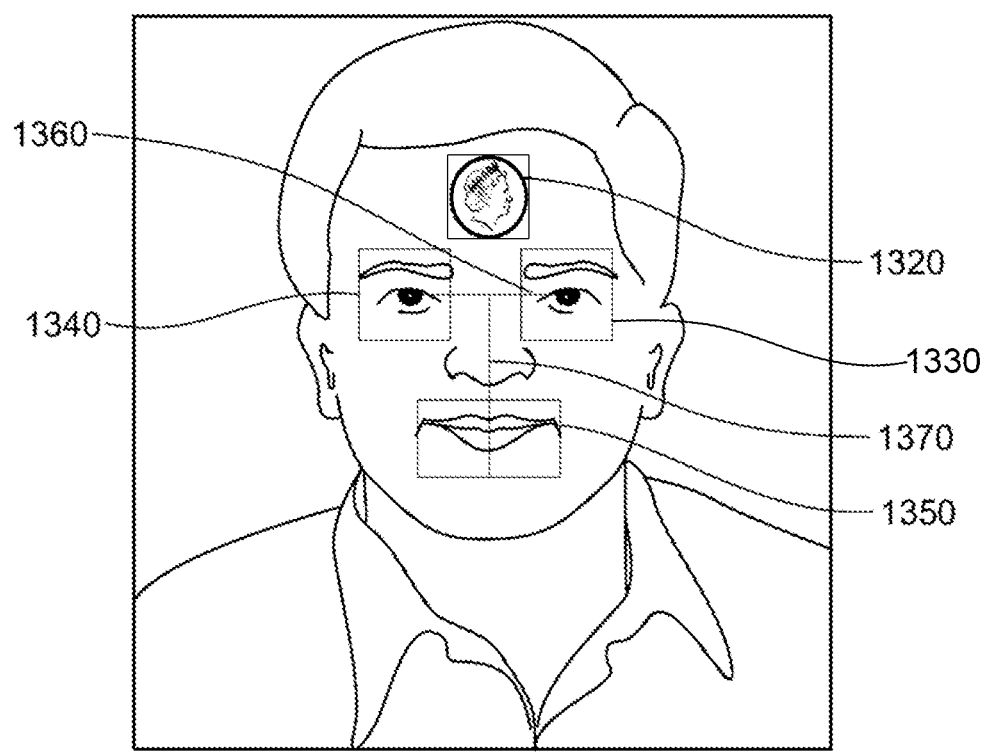
FIG. 13B is an illustration of the detected boxes and consequent facial feature measurement according to the method of FIG. 8.

FIG. 12 contains a flow chart illustrating a method 1200 that may be used to implement the facial feature measurement step 850 of the method 800 according to one implementation in which the facial feature measurement is face height. The method 1200 starts at step 1210, which draws an eyeline, i.e. a line between the centers of the two eye boxes selected at step 820. The eyeline is illustrated as the line 1360 in FIG. 13B, while the two eye boxes are illustrated as 1330 and 1340. Step 1220 determines a midpoint of the eyeline. Step 1230 then draws a midline from the midpoint found at step 1220 in a direction perpendicularly downwards from the eyeline found at step 1210. The midline drawn at step 1230 is illustrated as 1370 in FIG. 13B. Step 1240 then measures the face height as the length of the midline to the point where the midline intersects the bottom of the mouth box selected at step 820.

The face height measured at step 1240 may differ from the actual face height of the user because of a small rotation of the face around a horizontal axis. The ellipse found at step 840 can supply a correction for such a small horizontal rotation. The ratio of the true face height (in pixels) to the measured face height from step 1240 is the same as the ratio of the true height of the coin (in pixels) to the measured height of the ellipse from step 1160, if that height is smaller than the measured width (indicating horizontal rotation has taken place). Step 1250 therefore checks whether the measured height of the ellipse from step 1160 is less than the measured width, also from step 1160. If so ("Y"), the measured face height from step 1240 may be corrected for horizontal rotation at step 1260 by multiplying the measured face height by the ratio of the true height of the coin (in pixels) to the measured height of the ellipse from step 1160. The true height of the coin in pixels is simply the length of the major axis of the ellipse. An example of an ellipse for a detected coin is illustrated as 1320 in FIG. 13B. In the ellipse 1320, the width is less than the height, so there is no need for correction of the measured face height for horizontal rotation.

An alternative implementation of the method 800 makes use of an active shape model (ASM) [1] to detect the facial features at step 820. In general, an active shape model uses identified landmarks within a set of training images to develop a deformable model for the relative positions of the landmarks (the shape) and a statistical model of the pixel values provided by the images at those positions. The deformable shape model is defined as:

$$x = \bar{x} + Pb \quad \text{(Eq. 1)}$$

where x is a vector of landmark positions (the shape) as predicted by the model, x̄ is the mean shape, P is a set of eigenvectors also determined from the training set, and b is a vector of weights (the pose) allowing for the shape to be deformed. The statistical model of pixel values is determined by sampling a range of pixels normal to each landmark within each image in the training set. After sampling, a vector of mean pixel values is determined for each landmark as well as the corresponding covariance matrix. The pixel model for each landmark comprises the vector of mean pixel values and the corresponding covariance matrix.

Figure 14:
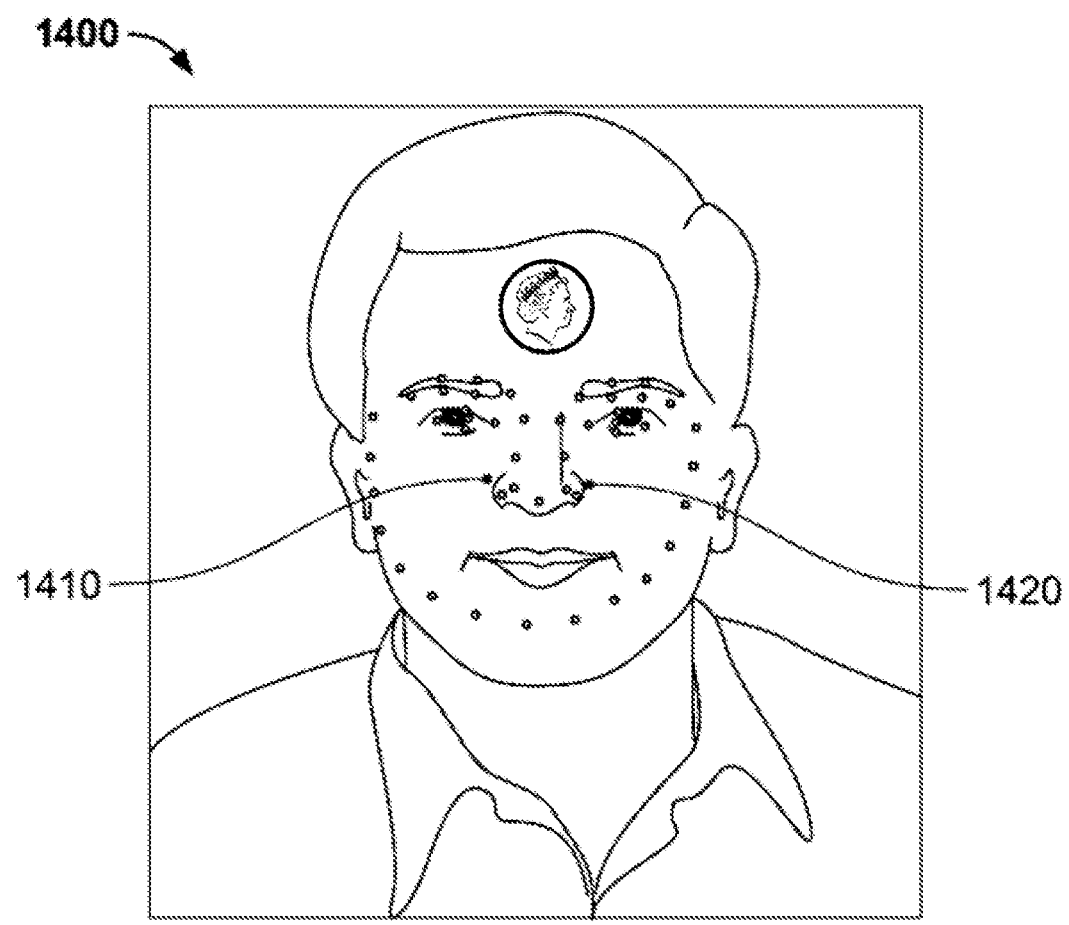
FIG. 14 is an illustration of the detected facial features in a captured image according to an alternative implementation of the method of FIG. 8.

The process of searching for landmarks in a captured image using an ASM is iterative. For the first iteration, the mean shape x̄ is used as the shape estimate x and is superimposed on the captured image in an initial location that is presumably not too far from the landmarks in the captured image, e.g. centred within the captured image. A range of pixel values are sampled at each landmark position in the captured image as defined by the current shape estimate x. The new estimated landmark positions are then selected by determining the range of pixels with the smallest Mahalanobis distance (covariance-weighted Euclidean distance) from the mean pixel values in the pixel model. The scale, translation and rotation of the shape estimate x are then updated to best match the new estimated landmark positions. Any residual error that remains is then used to deform the model by updating the current pose estimate b. The shape estimate x is then updated using Eq. 1. These steps are repeated until some high proportion (e.g. at least 90%) of the estimated landmark positions have converged within a small radius (e.g. 2 pixels) of the previous estimated positions; at this point the changes to shape scale, translation, rotation, and pose are presumed minimal. The convergence may be accelerated by repeating the iterative process over a three-level Gaussian pyramid with each level L containing a copy of the captured image decimated by $2^L$. Changes to landmark positions at coarse levels produce larger relative movements, and once shape convergence occurs, the iterative process moves up a level, producing finer changes in shape and pose. FIG. 14 illustrates the landmark positions identified by the iterative process in a typical captured image 1400.

In the implementation of the method 800 in which the ASM is used to implement step 820, the reference feature detection step 830 may initially use the cascade classifier described above in relation to step 902 to detect one or more "coin boxes", and then use the method 1000 described above to select the "best" detected coin.

In the alternative implementation of the method 800, the facial feature measurement step 850 measures the pixel distance between two selected landmarks that are suitable for sizing the mask. In one example illustrated in FIG. 14, suitable for sizing a nasal mask (see FIG. 1B), the selected landmarks are the left and right alar crest points 1410 and 1420 (see FIG. 3B), yielding a facial feature measurement of nose width.

8.4.4.2.2 Cornea

In a further implementation, the reference feature may be a feature of the eye(s) such as the iris or cornea of the user. Iris diameter is remarkably similar across all races, and does not grow after the early teens. The range of corneal diameters (horizontal visible iris diameter) is within 11.0 to 12.5 mm for 95% of adults [2]. The advantage of using the eye feature is that it obviates the need for an extraneous reference feature such as a coin, credit card, QR code etc. to be present in the captured image. In such an implementation, method 800 may be implemented as follows. The bounding points of one or each cornea may be detected as part of an ASM implementation of the facial feature detection step 820, in which the bounding points for each cornea are landmarks in the ASM. A separate reference feature detection step 830 would therefore not be required. Step 840 may compute the diameter of one or each cornea as the distance between the bounding points of the or each cornea, and compute the scaling factor as the ratio of the median corneal diameter of 11.75 mm to the measured corneal diameter (in pixels) for one or other eye, or the average of both measured corneal diameters. In a variation of step 840, the median corneal diameter is chosen based on knowledge of the user's age, since variation of corneal diameter across people of a given age is less than variation across the general adult population.

8.4.4.3 Assistant Mode

A mirror 330 is described above as being implemented to assist a user in capturing an image. However, the application for measuring and sizing may allow for alternatives. For example, processor 310, as controlled by the application, may provide the user with the option to use mirror 330 or a third party to hold sensor 340 and aim it directly at the intended mask user. Thus, the intended mask user may have his/her facial features and the reference feature captured by a relative, a friend, or a stationary stand that holds sensor 340. As such, the application may include a "partner" or "assistant" mode in which display interface 320 may present a live camera preview and a targeting box, such as camera live action preview 324 and targeting box 328. The application may then instruct the assistant on how to capture suitable images for mask sizing. For example, in this mode, processor 310 may optionally operate to allow the assistant to select the front facing camera or rear facing camera, which may be integrated into smartphone 234 or tablet 236. Thus, the assistant may look at display interface 320 and point the rear facing camera at the patient's facial features and a reference feature that may be held by the patient. "Partner" or "assistant" mode may also provide the user with the option to operate the front facing camera. Optionally, a stand can be used to hold the mobile device, while the user moves with respect to camera 340 until a reference feature held by the user is properly aligned within a target box displayed on display interface 320.

8.4.4.4 Lighting and Light Filters

It is also described above that if lighting conditions are unsatisfactory, processor 310, as controlled by the application, may notify the user that conditions are unsatisfactory and provide instructions for moving to a location of brighter or dimmer lighting. However, recognizing that satisfying this condition may not always be possible, the application may control the processor 310 to apply a light filter to the sensor/camera 340 to allow for operation in a wide array of lighting conditions. If the environment is too bright, a specific filter may be automatically applied so that the user's facial features can be easily detected. Conversely, where lighting conditions are too dark, another filter may be implemented to detect the desired facial features or the computing device's light source to illuminate the patient's facial features. This may be performed during the pre-capture phase 400.

8.4.4.5 Alternative Sensors

The method described herein is particularly useful for measuring and sizing based on two-dimensional images as cameras for two-dimensional images are ubiquitous. However, the disclosed technology contemplates other types of sensors that may be able to determine scale without the use of a reference feature, such as a laser and detector combination. For example, such a sensor may detect distance to the target, which can be used to calculate a scale. Other sensors may be utilized to obtain three-dimensional renderings. For example, a stereoscopic camera may be used to obtain a three-dimensional image. A similar process to that described above can be performed on the three-dimensional image. In such an embodiment, the reference feature can be a three dimensional object with known x, y, and z dimensions. Further sensors that can be used are a strobing light source and detector combination. Reflected light from the strobing light source can be timed to calculate distance in the processor.

8.4.4.6 Storage Mediums for the Application

In the exemplary method detailed above, the application for automatic facial feature measuring and patient interface sizing is downloaded to the computing device's internal memory from a third party server, such as an application-store server. However, in one embodiment, the application may be downloaded to the computing device's internal memory/data storage 350 via the network from server 210 or via some other external computer-readable storage medium, such as a flash drive, SD card or optical disc. Alternatively, in another embodiment, the application may be stored in an external computer-readable storage medium and directly linked to processor 310. In a further embodiment, the application including its corresponding processor instructions and data, may be stored on a medium external to computing device 230, such as server 210, and accessed by computing device 230 via a web browser (e.g., Google Chrome® or Internet Explorer®) and/or web browser extension such as Adobe Flash®.

8.4.4.7 Tracking & Updates

The application may include additional functionality such as tracking the user's weight over time and corresponding facial changes as the user's weight fluctuates, which may be integrated into the patient interface recommendation analysis. For example, weight, age and/or height may be a parameter that is considered in the data record for selection of the appropriate mask size. Additionally, the application may record the particular patient interfaces that the user/patient orders and the date that the order occurred so that replacement and/or maintenance reminders can be provided to the user via the application and/or for general health monitoring.

In addition, the application can be updated from time to time, which can be provided to users via an application store or server 210. These updates can provide users with new reference features and the known dimension information for the reference feature, updated mask sizing tables and new mask type information, and other data processing information, such as updated anthropometric correction factors, which can be can be continuously refined as more and more end users use the application and send their information back through server 210. Advantageously, the ability to update the reference feature remotely can enable more accurate measurements to be obtained or improve responsiveness of the application when subsequent reference features are developed. Remote updating may be a seamless background process that requires little or no user interaction, for example, the updating occurring when the application is loaded and an update is available. Remote updating of the application means that the subsequent versions of the application can also take advantage of more powerful, better or additional hardware components that are provided with newer models of computing device 230.

8.4.4.8 Other Image Sources

In an exemplary method described above, the images are captured by a sensor 340 such as a camera that is located on the same computing device 230 as the processor 310 that carries out the application 360 for facial feature measuring and patient interface sizing. However, in other implementations, the processor 310 may receive the images from another source over the network 220 to which the computing device 230 is connected. Examples of other sources include an MMS message, email, a web or other image server, e.g. the server 210. In still other implementations in which the server 210 carries out the application 360 for facial feature measuring and patient interface sizing, the server 210 may receive the images from another source over the network 220 to which the server 210 is connected.

8.5 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

As used herein, the terms "about," "generally" and "substantially" are intended to mean that deviations from absolute are included within the scope of the term so modified.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

8.6 Reference Label List patient 10
bed partner 20
capture 40
air circuit 50
humidifier 60
patient interface 100
plenum chamber 120
structure 130
vent 140
forehead support 150
seal-forming structure 160
connection port 170
system 200
server 210
network 220
network 222
wireless network 224
wireless link 226
computing device 230
laptop 232
webcam 233
smartphone 234
tablet 236
architecture 300
processor 310
display interface 320
display 320a
detection points 321
capture display 322
bounding boxes 323
live action preview 324
reference feature 326
status indicators 327
targeting box 328
reference feature image 329
mirror 330
user control/input interface 331
sensor 340
IMU 342
memory/data storage 350
instructions 352
stored data 354
application 360
pre-capture phase 400
step 410
step 420
step 430
step 440
step 450
image capture phase 500
step 510
step 520
post-image processing phase 600
step 610
step 620
step 630
step 640
step 650
step 660
step 670
step 680
output phase 700
step 710
step 720
step 730
step 732
method 800
step 810
step 820
step 830
step 840
step 850
step 860
step 870
step 880
method 900
step 902
step 905
step 910
step 915
step 920
step 925
step 930
step 935
step 940
step 945
step 950
step 955
step 960
method 1000
step 1010 step 1020
step 1030
step 1040
step 1050
step 1060
step 1070
step 1080
step 1090
method 1100
step 1105
step 1110
step 1115
step 1120
step 1130
step 1135
step 1140
step 1145
step 1150
step 1155
step 1160
step 1165
step 1170
step 1175
method 1200
step 1210
step 1220
step 1230
step 1240
step 1250
step 1260
coin 1300
forehead 1310
ellipse 1320
line 1360
captured image 1400
right alar crest point 1410
right alar crest point 1420

8.7 Cited References

[1] Cootes, T. F., Taylor, C. J., Cooper, D. H., & Graham, J. (1995). *Active Shape Models—Their Training and Application*. Computer Vision and Image Understanding, 61(1), 38-59.

[2] Florian Rufer, MD, Anke Schroder, MD, and Carl Erb, MD. *White-to-White Corneal Diameter: Normal Values in Healthy Humans Obtained With the Orbscan II Topography System*. Cornea, 24(3), 259-261, April 2005.

The invention claimed is:

1. A non-transitory computer-readable medium containing processor control instructions, which when executed by one or more processors, control operations for an automated method for selecting a patient interface according to patient interface size, the processor control instructions comprising:
instructions to control displaying a predetermined reference feature having a known dimension on a display interface of a display device;
instructions to receive image data captured by an image sensor coupled with the display device, the captured image data containing one or more facial features of an intended user of the patient interface in association with a displayed version of the predetermined reference feature being displayed on the display interface of the display device;
instructions to detect one or more facial features of the user in the captured image data;
instructions to detect the displayed version of the predetermined reference feature in the captured image data; and
instructions to process image pixel data of the captured image data to measure an aspect of the one or more facial features detected in the captured image data based on image pixel data associated with the displayed version of the predetermined reference feature and the known dimension of the predetermined reference feature.

2. The non-transitory computer-readable medium of claim 1 wherein the processor control instructions further comprise instructions to select a patient interface size from a group of standard patient interface sizes based on a comparison between the measured aspect of the one or more facial features and a data record relating sizing information of the group of standard patient interface sizes and the measured aspect of the one or more facial features.

3. The non-transitory computer-readable medium of claim 1 wherein the aspect of the one or more facial features comprises a distance between a sellion and supramenton of the user.

4. The non-transitory computer-readable medium of claim 1 wherein the instructions to process image pixel data comprise processing instructions to calculate a value of the measured aspect based on a scaling factor derived from the image pixel data associated with the displayed version of the predetermined reference feature.

5. The non-transitory computer-readable medium of claim 1 wherein the instructions to process image pixel data further comprise processing instructions to adjust a value of the measured aspect with an anthropometric correction factor.

6. The non-transitory computer-readable medium of claim 5 wherein the anthropometric correction factor is based on patient interface return data.

7. The non-transitory computer-readable medium of claim 1, wherein the display interface includes a targeting guide and a live action preview of content detected by the image sensor, the content including the displayed version of the predetermined reference feature being displayed on the display interface of the display device.

8. The non-transitory computer-readable medium of claim 7, wherein the processor control instructions comprise instructions to control capturing of the image data to satisfy at least one alignment condition.

9. The non-transitory computer-readable medium of claim 8, wherein the at least one alignment condition comprises detection of positioning of the displayed version of the predetermined reference feature of the live action preview within a box of the targeting guide.

10. The non-transitory computer-readable medium of claim 9, wherein the at least one alignment condition includes detection of a tilt condition being within about +/−10 degrees of a superior-inferior extending axis.

11. The non-transitory computer-readable medium of claim 10, wherein the at least one alignment condition includes detection of a tilt condition being within about +/−5 degrees of a superior-inferior extending axis.

12. The non-transitory computer-readable medium of claim 11, wherein detection of a tilt condition is performed by reading an inertial measurement unit (IMU).

13. The non-transitory computer-readable medium of claim 1 wherein the patient interface comprises a mask or nasal mask.

14. The non-transitory computer-readable medium of claim 1 wherein the instructions to process image pixel data comprise instructions to count pixels.

15. The non-transitory computer-readable medium of claim 2 wherein the processor control instructions further comprise instructions to control generating an automated electronic offer for a patient interface for purchase based on the selected patient interface size.

16. The non-transitory computer-readable medium of claim 1, wherein the processor control instructions further comprise instructions to calculate an average of the measured aspect of the facial feature from a plurality of captured images of the one or more facial features.

17. A system for automatically recommending a patient interface size complementary to a particular patient's facial features comprising:
one or more processors configured to:
display a predetermined reference feature having a known dimension on a display interface of a display device;
receive captured image data of an image, the captured image data containing one or more facial features of a user in association with a displayed version of the predetermined reference feature being displayed on the display interface of the display device, the image data captured with an image sensor that is coupled with the display device;
detect one or more facial features of the user in the captured image data;
detect the displayed version of the predetermined reference feature in the captured image data; and
process image pixel data of the captured image data to measure an aspect of the one or more facial features detected in the captured image data based on image pixel data associated with the displayed version of the predetermined reference feature and the known dimension of the predetermined reference feature.

18. The system of claim 17 wherein the one or more processors are further configured to select a patient interface size from a group of standard patient interface sizes based on a comparison between the measured aspect of the one or more facial features and a data record relating sizing information of the group of standard patient interface sizes and the measured aspect of the one or more facial features.

19. The system of claim 18 wherein the patient interface comprises a mask or nasal mask.

20. The system of claim 17 wherein the one or more processor comprises a mobile computing device, the mobile computing device configured to communicate with one or more servers over a network.

21. The system of claim 17 wherein the one or more processors comprises one or more servers.

22. The system of claim 21 wherein the one or more servers is configured to transfer by download to a computing device comprising a mobile device processor of the one or more processors, via a network, processor control instructions for operating the mobile device processor for automatically recommending a patient interface size complementary to a particular patient's facial features.

23. Apparatus for automatically recommending a patient interface size complementary to a particular patient's facial features, the apparatus comprising:
means for displaying a predetermined reference feature having a known dimension;
means for receiving image data captured by an image sensor, the captured image data containing one or more facial features of an intended user of the patient interface in association with a displayed version of the predetermined reference feature being displayed on the means for displaying;
means for detecting one or more facial features of the user in the captured image data;
means for detecting the displayed version of the predetermined reference feature in the captured image data; and
means for processing image pixel data of the captured image data to measure an aspect of the one or more facial features detected in the captured image data based on image pixel data associated with the displayed version of the predetermined reference feature and the known dimension of the predetermined reference feature.

24. The apparatus of claim 23 further comprising:
means for selecting a patient interface size from a group of standard patient interface sizes based on a comparison between the measured aspect of the one or more facial features and a data record relating sizing information of the group of standard patient interface sizes and the measured aspect of the one or more facial features.

* * * * *